United States Patent
Danielsson et al.

(10) Patent No.: US 10,575,800 B2
(45) Date of Patent: Mar. 3, 2020

(54) INCREASED SPATIAL RESOLUTION FOR PHOTON-COUNTING EDGE-ON X-RAY DETECTORS

(71) Applicant: Prismatic Sensors AB, Stockholm (SE)

(72) Inventors: Mats Danielsson, Taby (SE); Jacob J Wikner, Linkoping (SE)

(73) Assignee: PRISMATIC SENSORS AB, Stockholm (SE)

( * ) Notice: Subject to any disclaimer, the term of this patent is extended or adjusted under 35 U.S.C. 154(b) by 454 days.

(21) Appl. No.: 15/453,315

(22) Filed: Mar. 8, 2017

(65) Prior Publication Data
US 2018/0256121 A1 Sep. 13, 2018

(51) Int. Cl.
| | | |
|---|---|---|
| *A61B 6/00* | (2006.01) | |
| *G01T 1/24* | (2006.01) | |
| *G01B 15/04* | (2006.01) | |
| *A61B 6/03* | (2006.01) | |

(52) U.S. Cl.
CPC .......... *A61B 6/4241* (2013.01); *G01B 15/045* (2013.01); *G01T 1/24* (2013.01); *A61B 6/032* (2013.01); *A61B 6/482* (2013.01); *A61B 6/502* (2013.01)

(58) Field of Classification Search
CPC ......... G01T 1/24; A61B 6/4241; A61B 6/032; A61B 6/482; A61B 6/582; G01B 15/045
USPC ....... 250/370.09, 370.08, 370.01, 371, 370.1
See application file for complete search history.

(56) References Cited

U.S. PATENT DOCUMENTS

| | | | | |
|---|---|---|---|---|
| 4,937,453 A | * | 6/1990 | Nelson | G01T 1/2018 250/370.09 |
| 5,434,417 A | * | 7/1995 | Nygren | G01T 1/242 250/370.01 |
| 6,169,287 B1 | | 1/2001 | Warburton | |
| 6,512,838 B1 | * | 1/2003 | Rafii | G01C 3/08 348/E3.018 |
| 7,009,183 B2 | | 3/2006 | Wainer et al. | |
| 7,208,740 B2 | | 4/2007 | El-Hanany et al. | |
| 7,692,155 B2 | | 4/2010 | He et al. | |
| 8,063,380 B2 | | 11/2011 | Levin et al. | |

(Continued)

FOREIGN PATENT DOCUMENTS

WO 2016/076767 A1 5/2016

OTHER PUBLICATIONS

Magnus Åslund, et al., Physical characterization of a scanning photon counting digital mammography system based on Si-strip detectors, Medical Physics, Jun. 2007, pp. 1918-1925, vol. 34, No. 6, American Association of Physicists in Medicine.

(Continued)

*Primary Examiner* — David P Porta
*Assistant Examiner* — Blake C Riddick
(74) *Attorney, Agent, or Firm* — Young & Thompson

(57) ABSTRACT

There is provided a method and an arrangement for determining a position of interaction of a photon in an individual detector diode of a photon-counting x-ray detector. The method includes determining the position of interaction in the detector diode based on pulse characteristics of a pulse generated by the individual detector diode in response to the photon interaction.

20 Claims, 28 Drawing Sheets

(56) References Cited

U.S. PATENT DOCUMENTS

| | | |
|---|---|---|
| 8,183,535 B2 | 5/2012 | Danielsson et al. |
| 9,867,580 B2 | 1/2018 | Danielsson et al. |
| 2002/0018543 A1* | 2/2002 | Danielsson .......... G01T 1/1644 378/98.8 |
| 2002/0117626 A1* | 8/2002 | Danielsson ....... H01L 27/14623 250/370.01 |
| 2008/0042070 A1* | 2/2008 | Levin ...................... H04N 5/32 250/370.13 |
| 2008/0169421 A1* | 7/2008 | Danielsson .......... G01T 1/1648 250/370.09 |
| 2010/0025589 A1 | 2/2010 | Olcott et al. |
| 2010/0127178 A1 | 5/2010 | Laurence et al. |
| 2010/0204942 A1* | 8/2010 | Danielsson ............. G01T 1/242 702/85 |
| 2010/0215230 A1* | 8/2010 | Bornefalk ............. G06T 11/005 382/128 |
| 2010/0270462 A1* | 10/2010 | Nelson ................. G01T 1/2018 250/252.1 |
| 2014/0110592 A1* | 4/2014 | Nelson ................. G01T 1/1611 250/370.09 |
| 2014/0353510 A1 | 12/2014 | Spanoudaki et al. |
| 2016/0259067 A1* | 9/2016 | Morton ................. G01T 1/2018 |
| 2018/0224564 A1* | 8/2018 | Fu ........................... G01T 1/247 |

OTHER PUBLICATIONS

Matthew G. Wallis, et al., Two-View and Single-View Tomosynthesis versus Full-Field Digital Mammography: High-Resolution X-Ray Imaging Observer Study, Radiology, Mar. 2012, pp. 788-796, vol. 262, No. 3.

Bjorn Cederstrom, et al., High-resolution X-ray imaging using the signal time dependence on a double-sided silicon detector, Nuclear Instruments and Methods in Physics Research, 1999, pp. 135-145, vol. 423, No. 1, Elsevier Science B.V.

Xuejin Liu, et al., Energy Calibration of a Silicon-Strip Detector for Photon-Counting Spectral CT by Direct Usage of the X-ray Tube Spectrum, IEEE Transactions on Nuclear Science, Feb. 2015, pp. 68-75, vol. 62, No. 1.

International Search Report and Written Opinion, dated Apr. 27, 2018, from corresponding PCT application No. PCT/SE2018/050095.

* cited by examiner

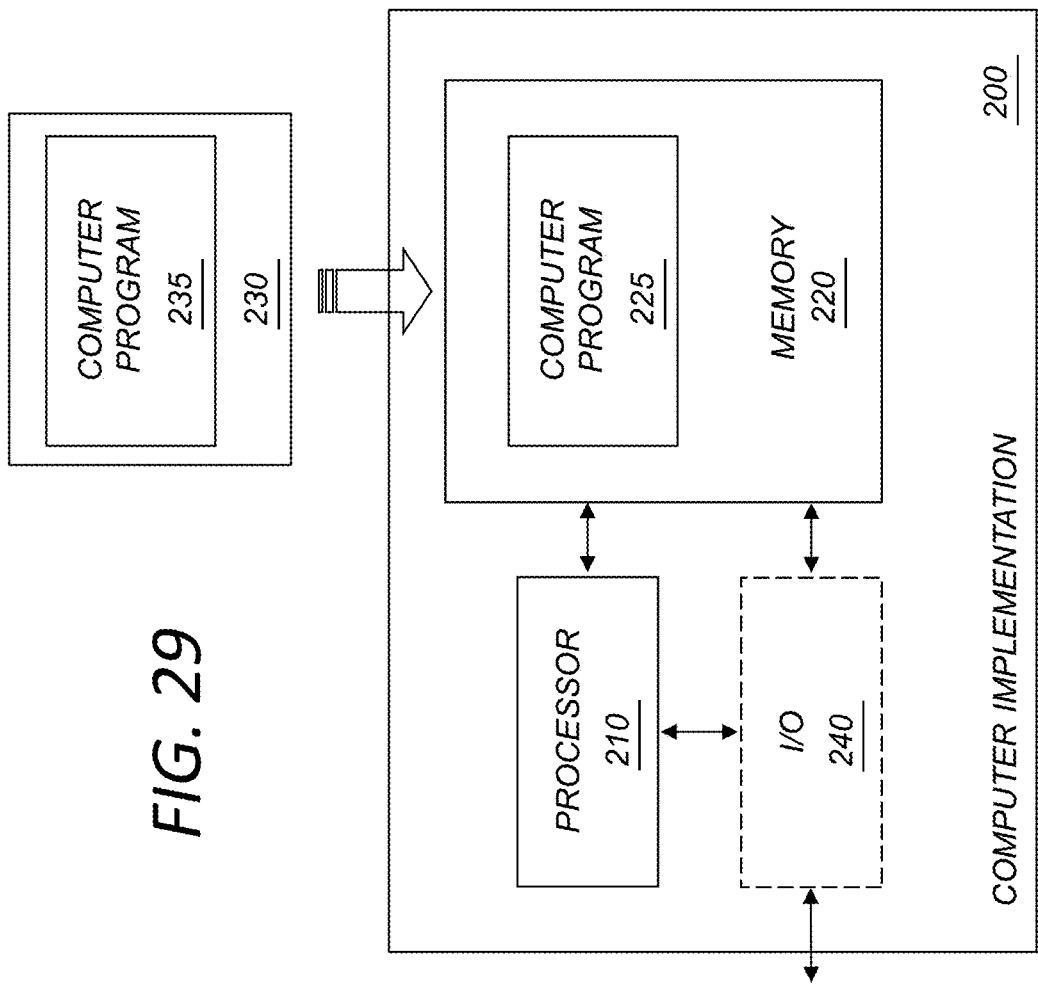

INCREASED SPATIAL RESOLUTION FOR PHOTON-COUNTING EDGE-ON X-RAY DETECTORS

TECHNICAL FIELD

The proposed technology relates to radiographic imaging such as x-ray imaging and related x-ray detector systems. In particular, the proposed technology concerns a method and arrangement for determining a position of interaction of a photon in an individual detector diode of a photon-counting x-ray detector, as well as a corresponding x-ray detector system and x-ray imaging system.

BACKGROUND

Radiographic imaging such as x-ray imaging has been used for years in medical applications and for non-destructive testing.

Normally, an x-ray imaging system includes an x-ray source and an x-ray detector system. The x-ray source emits x-rays, which pass through a subject or object to be imaged and are then registered by the x-ray detector system. Since some materials absorb a larger fraction of the x-rays than others, an image is formed of the subject or object.

It may be useful to begin with a brief overview of an illustrative overall x-ray imaging system, with reference to FIG. 1. In this non-limiting example, the x-ray imaging system 100 basically comprises an x-ray source 10, an x-ray detector system 20 and an associated image processing device 30. In general, the x-ray detector system 20 is configured for registering radiation from the x-ray source 10 that may have been focused by optional x-ray optics and passed an object or subject or part thereof. The x-ray detector system 20 is connectable to the image processing device 30 via suitable analog processing and read-out electronics (which may be integrated in the x-ray detector system 20) to enable image processing and/or image reconstruction by the image processing device 30.

A challenge for x-ray imaging detectors is to extract maximum information from the detected x-rays to provide input to an image of an object or subject where the object or subject is depicted in terms of density, composition and structure. It is still common to use film-screen as detector but mostly the detectors today provide a digital image.

Modern x-ray detectors normally need to convert the incident x-rays into electrons, this typically takes place through photo absorption or through Compton interaction and the resulting electrons are usually creating secondary visible light until its energy is lost and this light is in turn detected by a photo-sensitive material. There are also detectors, which are based on semiconductors and in this case the electrons created by the x-ray are creating electric charge in terms of electron-hole pairs which are collected through an applied electric field.

There are detectors operating in an integrating mode in the sense that they provide an integrated signal from a multitude of x-rays and the signal is only later digitized to retrieve a best guess of the number of incident x-rays in a pixel.

Photon counting detectors have also emerged as a feasible alternative in some applications; currently those detectors are commercially available mainly in mammography. The photon counting detectors have an advantage since in principal the energy for each x-ray can be measured which yields additional information about the composition of the object. This information can be used to increase the image quality and/or to decrease the radiation dose.

Compared to the energy-integrating systems, photon-counting CT has the following advantages. Firstly, electronic noise that is integrated into signal by the energy-integrating detectors can be rejected by setting the lowest energy threshold above the noise floor in the photon-counting detectors. Secondly, energy information can be extracted by the detector, which allows improving contrast-to-noise ratio by optimal energy weighting and which also allows so-called material basis decomposition, by which different components in the examined patient can be identified and quantified, to be implemented effectively. Thirdly, more than two basis materials can be used which benefits decomposition techniques, such as K-edge imaging whereby distribution of contrast agents, e.g. iodine or gadolinium, are quantitatively determined. Fourth, there is no detector afterglow, meaning that high angular resolution can be obtained. Last but not least, higher spatial resolution can be achieved by using smaller pixel size.

The most promising materials for photon-counting x-ray detectors are cadmium telluride (CdTe), cadmium zinc telluride (CZT) and silicon (Si). CdTe and CZT are employed in several photon-counting spectral CT projects for the high absorption efficiency of high-energy x-rays used in clinical CT. However, these projects are slowly progressing due to several drawbacks of CdTe/CZT. CdTe/CZT have low charge carrier mobility, which causes severe pulse pileup at flux rates ten times lower than those encountered in clinical practice. One way to alleviate this problem is to decrease the pixel size, whereas it leads to increased spectrum distortion as a result of charge sharing and K-escape. Also, CdTe/CZT suffer from charge trapping, which would lead to polarization that causes a rapid drop of the output count rate when the photon flux reaches above a certain level.

In contrast, silicon has higher charge carrier mobility and is free from the problem of polarization. The mature manufacturing process and comparably low cost are also its advantages. But silicon has limitations that CdTe/CZT does not have. Silicon sensors must accordingly be quite thick to compensate for its low stopping power. Typically, a silicon sensor needs a thickness of several centimeters to absorb most of the incident photons, whereas CdTe/CZT needs only several millimeters. On the other hand, the long attenuation path of silicon also makes it possible to divide the detector into different depth segments, as will be explained below. This in turn makes it possible for a silicon-based photon-counting detector to properly handle the high fluxes in CT.

When using simple semiconductor materials, as silicon or germanium, Compton scattering causes many x-ray photons to convert from a high energy to a low energy before conversion to electron-hole pairs in the detector. This results in a large fraction of the x-ray photons, originally at a higher energy, producing much less electron-hole pairs than expected, which in turn results in a substantial part of the photon flux appearing at the low end of the energy distribution. In order to detect as many of the x-ray photons as possible, it is therefore necessary to detect as low energies as possible.

Indeed, photon counting x-ray imaging has gained considerable attention the last decade and in some cases matured into clinical applications. In order to increase the absorption efficiency, the detector can be arranged edge-on, in which case the absorption depth can be chosen to any length and the detector can still be fully depleted without going to very high voltages. For example, reference can be made to "Physical characterization of a scanning photon counting digital mammography system based on Si-strip detectors" by M. Åslund, B. Cederström, M. Lundqvist, and M. Danielsson in Med. Phys. 34, 2007, and "Two-View and Single-View Tomosynthesis versus Full-Field Digital Mammography: High-Resolution X-Ray Imaging Observer Study" by M G. Wallis, E. Moa, F. Zanca, K. Leifland and M. Danielsson in *Radiology,* 2012 Jan. 31.

U.S. Pat. No. 8,183,535 discloses an example of a photon-counting edge-on x-ray detector. In this patent, there are multiple semiconductor detector modules arranged together to form an overall detector area, where each semiconductor detector module comprises an x-ray sensor oriented edge-on to incoming x-rays and connected to integrated circuitry for registration of x-rays interacting in the x-ray sensor.

Photon-counting detectors based on direct conversion in simple semiconductor detectors, for example based on silicon or germanium, are well-known. For example, the use of a silicon diode for high-performance x-ray detectors is though less commonly used due to the more attractive features of e.g. CZT. A silicon diode is however cheaper to implement, but may require more signal processing.

Normally, the resolution is determined by the pitch of the diodes in one dimension and in the other dimension by the thickness of the wafer. Both the pitch for the diodes and the wafer thickness can be changed but to change the wafer thickness comes with a cost penalty and at some point, the wafers will be so thin that it will be hard or impossible to assemble the edge-on detectors without dead space between active areas.

Another possibility is to look at the time difference for the signal to reach the respective side of the wafers, the anode for the electrons and the cathode for the holes. This was studied and reported in "High resolution x-ray imaging using the signal time dependence on a double-sided silicon detector" by B. Cederström, M. Danielsson, M. Lundqvist and D. Nygren in Nucl. Instr. and Meth, 423 (1), pp. 135-145, 1999. The drawback with this arrangement is that it is impractical to combine the signals from the two sides of the wafer. The number of interconnects will increase dramatically.

The reference "Energy Calibration of a Silicon-Strip Detector for Photon-Counting Spectral CT by Direct Usage of the X-ray Tube Spectrum", by Xuejin Liu, 2015 relates to a method by which a detector can be calibrated for variations in the silicon diode's physical properties by trimming the energy levels from a known source, and measure reference levels for comparison.

However, there is still room for improvements relating to the issue of increasing the resolution of photon-counting x-ray detectors.

SUMMARY

It is an object to provide a method for determining a position of interaction of a photon in an individual detector diode of a photon-counting x-ray detector.

It is also an object to provide an arrangement configured to determine a position of interaction of a photon in an individual detector diode of a photon-counting x-ray detector.

Another object is to provide an x-ray detector system comprising such an arrangement.

Yet another object is to provide an x-ray imaging system comprising such an arrangement.

These objects are met by embodiments of the invention.

According to a first aspect, there is provided a method for determining a position of interaction of a photon in an individual detector diode of a photon-counting x-ray detector, characterized by determining the position of interaction in the detector diode based on pulse characteristics of a pulse generated by the individual detector diode in response to the photon interaction.

According to a second aspect, there is provided an arrangement configured to determine a position of interaction of a photon in an individual detector diode of a photon-counting x-ray detector, characterized in that the arrangement is configured to determine the position of interaction in the detector diode based on pulse characteristics of a pulse generated by the individual detector diode in response to the photon interaction.

According to a third aspect, there is provided an x-ray detector system comprising such an arrangement.

According to a fourth aspect, there is provided an x-ray imaging system comprising such an arrangement.

A basic idea is thus to determine where (for example on which side) a photon enters/impacts/interacts with the diode based on the pulse characteristics of the pulse generated by the diode in response to the photon interaction. The position of the interaction can be estimated from the pulse generated at one side, i.e. the cathode side or anode side.

By detecting which type of pulse that is arriving from the diode, additional information about the locality of the photon impact can be obtained, which will increase the resolution.

Preferably, the position of interaction may be determined by performing signal processing of the pulse based on at least one matched filter, as explained later on.

By way of example, the position of interaction may be determined by performing signal processing of the pulse based on at least two matched filters that are configured for mimicking the characteristic responses for different positions or sub-regions of photon interaction in the detector diode.

Other aspects and/or advantages will be appreciated when reading the following description.

BRIEF DESCRIPTION OF THE DRAWINGS

FIG. 29 is a schematic diagram illustrating an example of a computer-implementation according to an embodiment.

DETAILED DESCRIPTION

For a better understanding it may be useful to start with a somewhat more detailed overview of x-ray imaging systems and x-ray detectors.

Figure 2:
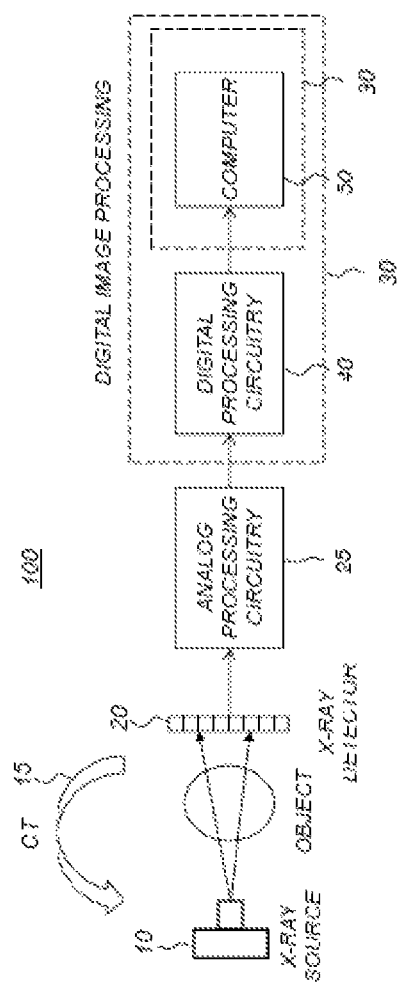
FIG. 2 is a schematic diagram illustrating another example of an x-ray imaging system.

FIG. 2 is a schematic diagram illustrating another example of an x-ray imaging system. In this example, the x-ray imaging system 100 comprises an x-ray source 10, which emits x-rays; an x-ray detector system 20, which detects the x-rays after they have passed through the object; analog processing circuitry 25, which processes the raw electrical signal from the detector and digitizes it; digital processing circuitry 40 which may carry out further processing operations on the measured data such as applying corrections, storing it temporarily, or filtering; and a computer 50 which stores the processed data and may perform further post-processing and/or image reconstruction.

The overall detector may be regarded as the x-ray detector system 20, or the x-ray detector system 20 combined with the associated analog processing circuitry 25.

A modern x-ray detector typically comprises one or more semiconducting devices that upon excitation by a photon is absorbed and generates a current flow through a diode for a short period of time.

The digital part including the digital processing circuitry 40 and/or the computer 50 may be regarded as a digital image processing system 30, which performs image reconstruction based on the image data from the x-ray detector. The image processing system 30 may thus be seen as the computer 50, or alternatively the combined system of the digital processing circuitry 40 and the computer 50, or possibly the digital processing circuitry 40 by itself if the digital processing circuitry is further specialized also for image processing and/or reconstruction.

An example of a commonly used x-ray imaging system is a Computed Tomography (CT) system, which may include an x-ray source that produces a fan or cone beam of x-rays and an opposing x-ray detector system for registering the fraction of x-rays that are transmitted through a patient or object. The x-ray source and detector system are normally mounted in a gantry that rotates around the imaged object.

Accordingly, the x-ray source 10 and the x-ray detector system 20 illustrated in FIG. 2 may thus be arranged as part of a CT system, e.g. mountable in a CT gantry.

Figure 3:
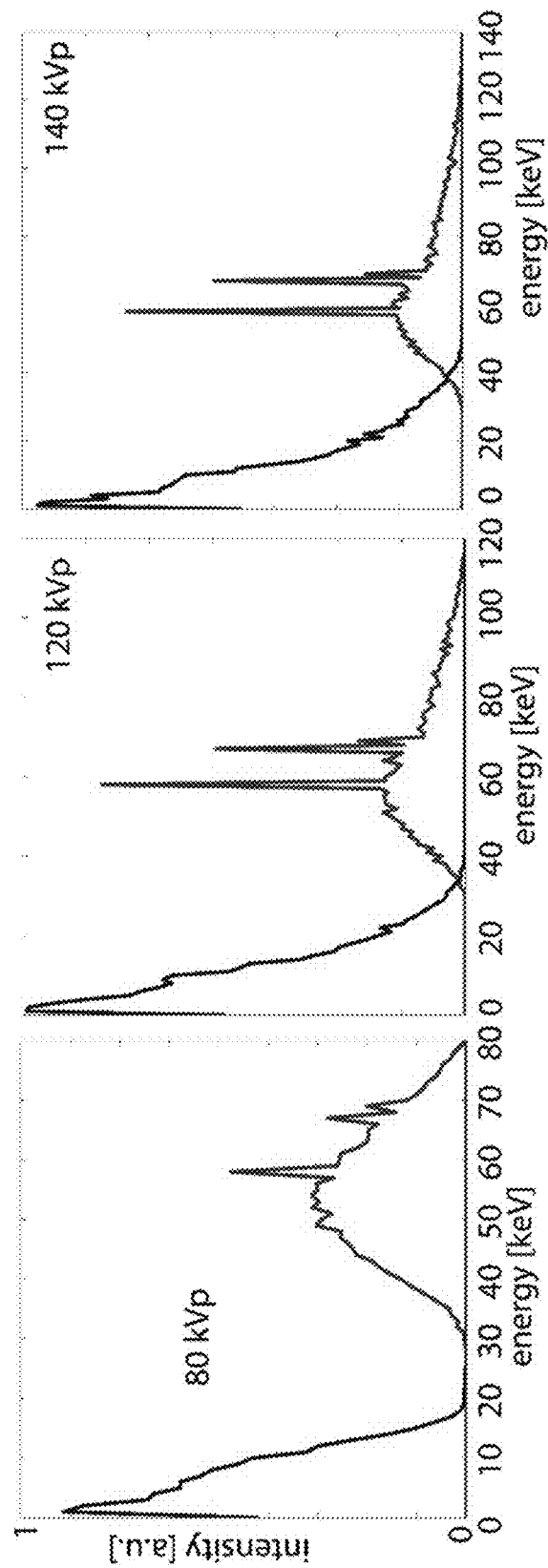
FIG. 3 is a schematic diagram illustrating examples of the energy spectrum for three different x-ray tube voltages.

FIG. 3 is a schematic diagram illustrating examples of the energy spectrum for three different x-ray tube voltages. The energy spectrum is built up by deposited energies from a mix of different types of interactions, including Compton events at the lower energy range and photoelectric absorption events at the higher energy range.

A further development of x-ray imaging is energy-resolved x-ray imaging, also known as spectral x-ray imaging, where the x-ray transmission is measured for several different energy levels. This can be achieved by letting the source switch rapidly between two different emission spectra, by using two or more x-ray sources emitting different x-ray spectra, or by using an energy-discriminating detector which measures the incoming radiation in two or more energy levels, also referred to as energy bins.

In the following, a brief description of an example of an energy-discriminating photon-counting mechanism is given with reference to FIG. 4. In this example, each registered photon generates a current pulse which is compared to a set of thresholds, thereby counting the number of photons incident in each of a number of energy bins.

In general, the x-ray photons, including also photons after Compton scattering, are converted to electron-hole pairs inside the semiconductor detector, where the number of electron-hole pairs is generally proportional to the photon energy. The electrons and holes are then drifting towards the detector electrodes, then leaving the detector.

Figure 4:
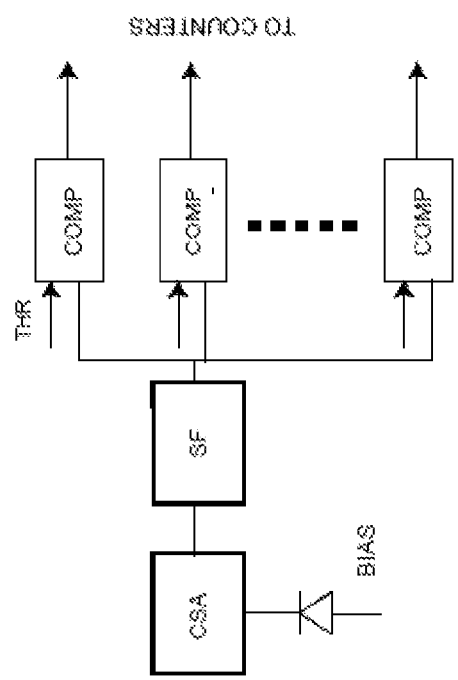
FIG. 4 is a schematic diagram illustrating an example of a photon counting mechanism.

During this drift, the electrons and holes induce an electrical current in the electrode, a current which may be measured, e.g. through a Charge Sensitive Amplifier (CSA), followed by a Shaping Filter (SF), as schematically illustrated in FIG. 4.

As the number of electrons and holes from one x-ray event is proportional to the x-ray energy, the total charge in one induced current pulse is proportional to this energy. The current pulse is amplified in the CSA and then filtered by the SF filter. By choosing an appropriate shaping time of the SF filter, the pulse amplitude after filtering is proportional to the total charge in the current pulse, and therefore proportional to the x-ray energy. Following the SF filter, the pulse amplitude is measured by comparing its value with one or several threshold values (Thr) in one or more comparators (COMP), and counters are introduced by which the number of cases when a pulse is larger than the threshold value may be recorded. In this way it is possible to count and/or record the number of X-ray photons with an energy exceeding an energy corresponding to respective threshold value (Thr) which has been detected within a certain time frame.

When using several different threshold values, a so-called energy-discriminating detector is obtained, in which the detected photons can be sorted into energy bins corresponding to the various threshold values. Sometimes, this type of detector is also referred to as a multi-bin detector.

In general, the energy information allows for new kinds of images to be created, where new information is available and image artifacts inherent to conventional technology can be removed.

In other words, for an energy-discriminating detector, the pulse heights are compared to a number of programmable thresholds in the comparators and classified according to pulse-height, which in turn is proportional to energy.

Figure 5:
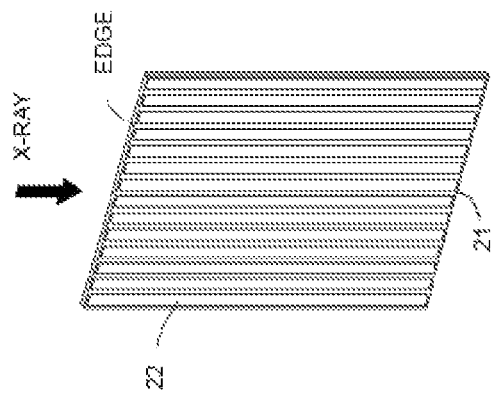
FIG. 5 is a schematic diagram illustrating an example of a semiconductor detector module according to an exemplary embodiment.

FIG. 5 is a schematic diagram illustrating an example of a semiconductor detector module according to an exemplary embodiment. This is an example of a semiconductor detector module with the sensor area 21 split into detector elements 22, corresponding to pixels, where each detector element or pixel is normally based on a diode. The x-rays enter through the edge of the semiconductor sensor.

Figure 6:
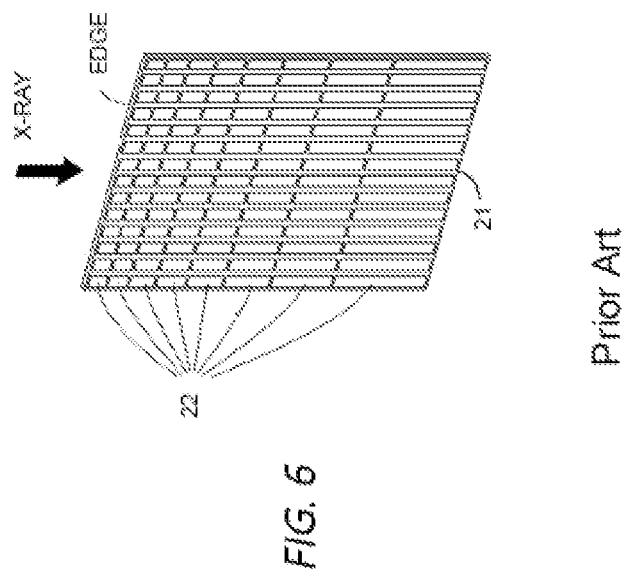
FIG. 6 is a schematic diagram illustrating an example of semiconductor detector module according to another exemplary embodiment.

FIG. 6 is a schematic diagram illustrating an example of semiconductor detector module according to another exemplary embodiment. In this example, the semiconductor sensor area 21 is further split into so-called depth segments 22 in the depth direction, again assuming the x-rays enter through the edge.

The semiconductor sensors may be implemented as so called Multi-Chip Modules (MCMs) in the sense that the semiconductor sensors are used as base substrates for electric routing and for a number of Application Specific Integrated Circuits (ASICs) which are attached preferably through so called flip-chip technique. The routing will include a connection for the signal from each pixel to the ASIC input as well as connections from the ASIC to external memory and/or digital data processing. Power to the ASICs may be provided through similar routing taking into account the increase in cross-section which is required for the large currents in these connections, but the power may also be provided through a separate connection. The ASICS may be positioned on the side of the active sensor and this means it can be protected from the incident x-rays if an absorbing cover is placed on top and it can also be protected from scattered x-rays from the side by positioning an absorber also in this direction.

Figure 7:
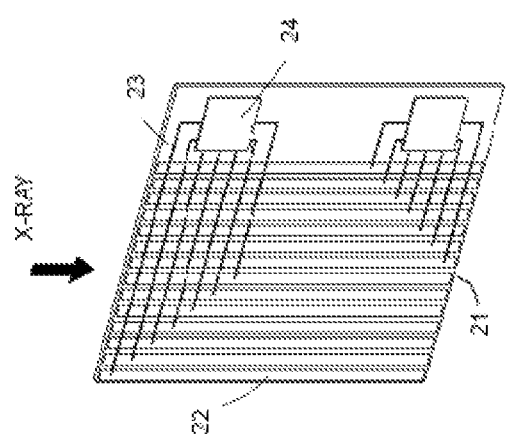
FIG. 7 is a schematic diagram illustrating an example of a semiconductor detector module according to yet another exemplary embodiment.

FIG. 7 is a schematic diagram illustrating an example of a semiconductor detector module. In this example, it is illustrated how the sensor area 21 of the semiconductor detector (module) 20 also can have the function of substrate in a Multi-Chip Module (MCM), similar to embodiments in U.S. Pat. No. 8,183,535. The signal is routed by signal paths 23 from the pixels 22 to inputs of parallel processing circuits 24 (e.g. ASICs) that are positioned next to the active sensor area. It should be understood that the term Application Specific Integrated Circuit (ASIC) is to be interpreted broadly as any general integrated circuit used and configured for a specific application. The ASICs process the electric charge generated from each x-ray and converts it to digital data which can be used to detect a photon and/or estimate the energy of the photon. The ASICs may be configured for connection to digital processing circuitry and/or memories located outside of the MCM and finally the data will be used as input for reconstructing an image.

Normally, a pixel is a single x-ray sensitive sub-element of the detector. Each pixel measures the incident x-ray flux as a sequence of frames. A frame is the measured data during a specified time interval (normally called a frame time).

Figure 8:
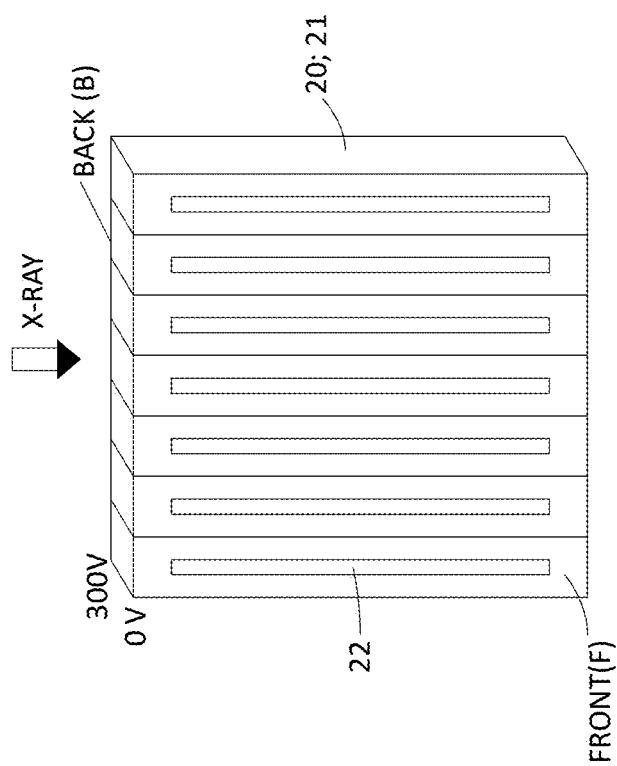
FIG. 8 is a schematic diagram illustrating an example of a detector (module) with a plurality of electrodes or detector elements.

FIG. 8 is a schematic diagram illustrating an example of a detector (module) with a plurality of electrodes or detector elements. In this example, the electrodes or detector elements 22 are arranged in parallel, where each detector element is made up by a detector diode. FIG. 8 shows how x-rays enter from the top and hits the active detector area in one (or many) of the detector elements 22 corresponding to pixels (picture elements). We refer to the front side (F) and the backside (B) of the detector (modules). On the front-side, the detector (module) is connected to the ground potential (0 V). On the back-side the detector (module) is connected to a much higher potential (e.g. ranging from 100 to 500 V, and here indicated as 300 V).

Figure 9:
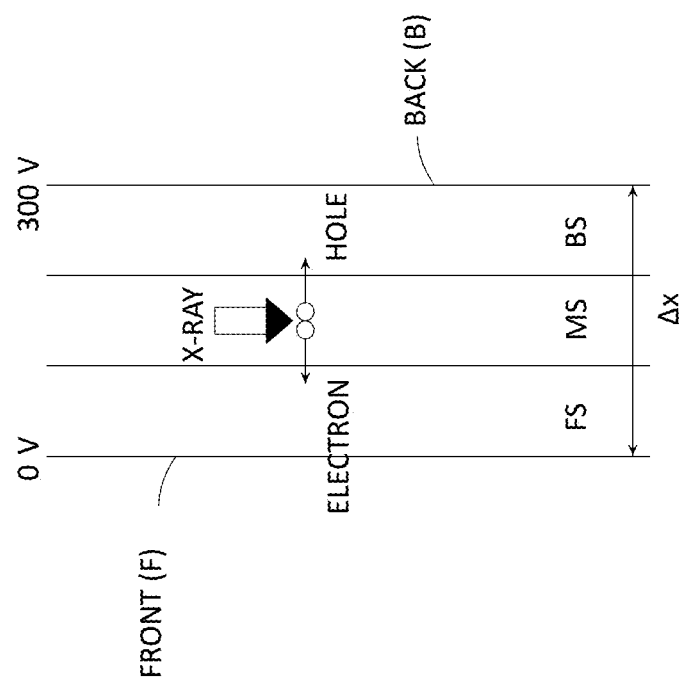
FIG. 9 is a schematic diagram illustrating an example of a cross-section of a detector element or pixel.

FIG. 9 is a schematic diagram illustrating an example of a cross-section of a detector diode. The detector diode can be divided into an arbitrary number $N \geq 2$ of sections from the front side (F) to the back side (B), such as a front-section (FS), a middle section (MS) and back section (BS). It should be understood that the selected number N of sections could be two or any higher number, as desired. The front section (FS) may coincide with the front side (F) and the back section (BS) may coincide with the back side (B).

In this particular example, a photon excites a hole and electron pair and the impact/absorption occurs in the middle section (MS), but could in general occur anywhere between the front-side (F) to the back-side (B). The thickness of the wafer is indicated by the parameter $\Delta x$.

The corresponding flow of charges thereby generated in the detector element is referred to as a pulse. In general, the shapes, durations and amplitudes of these pulses typically depend on the energy, position (angle), and intensity of the incoming x-rays.

As mentioned, the current can be detected by sensitive analog circuitry in different ways. There could be a measuring device that monitors and amplifies the currents generated by the photons. The amplified current could be compared to one or more threshold levels and then digitally indicating the occurrence of a photon.

The detector could also be designed to integrate the current on a capacitor to form a voltage according to:

$$v(t) = C \cdot \int i_{diode}(t) dt \qquad (1)$$

enabling the use of a voltage-mode detection circuit, which typically is easier to realize in standard available hardware. There could further be hybrids of these two conceptual approaches, where, for example, the pulses are compared with a multitude of threshold levels, or reference levels, such that the energy levels of the pulses can be determined and used to analyze the pulses. Another reason for using a hybrid is to be able to trade between noise immunity and speed.

As indicated in FIG. 9, there exists a concept of locality of absorption in the detector diode in the line of thickness of the diode or wafer, e.g. as indicated by the back section (BS), middle section (MS) and front section (FS) of FIG. 9. The inventors have realized that the current pulses generated upon absorption of a photon in the diode describe different electrical properties/pulse shapes, especially dependent on where the photon is absorbed in the detector diode (e.g. which side of the diode/pixel).

Figure 10:
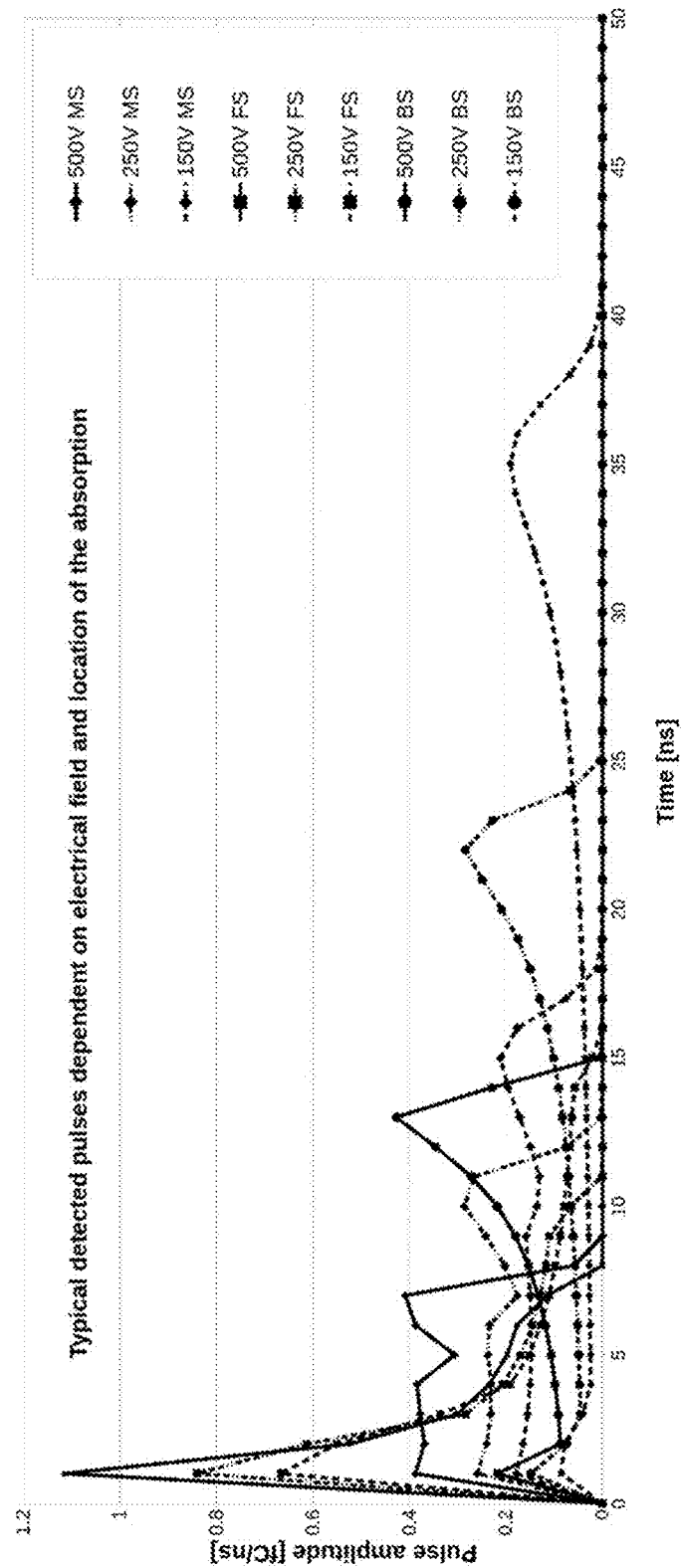
FIG. 10 is a schematic diagram illustrating an example of the shapes of different kinds of pulses for different physical and electrical properties of the diode.

FIG. 10 is a schematic diagram illustrating an example of the shapes of different kinds of pulses for different physical and electrical properties of the diode. In other words, these are examples of typical waveforms of the detector pulses (currents) as they enter the x-ray detector read-out circuitry. The absolute numbers are in this context not important, but the pulses duration may span over some 40 ns for a typical detector implementation. Nine simulated waveforms for different voltages applied across the diode (150V: dashed, 250V: dash-dotted, and 500V: solid) and for three different locations of absorption (MS: middle section, diamond, FS: front-section/front-side, square, and BS: back-section/back-side, circle).

On the vertical axis we display the charge flow per second in fC/ns, i.e., the current, and on the horizontal axis we have the time. The front-side pulses show a much faster behavior than the back-side ones. The front-side pulses (left-most and upper-most in the figure) have a sharp transition to its peak amplitude (maximum current) and then decreasing fairly rapidly. The back-side pulses show a comparatively slow increase towards a peak value at the end of the pulse instead.

Notice that the total charge, i.e., the integrated pulse, is the same for all pulses of same voltage. The total charge increases with voltage (150V, 250V, 500V in the figure). The total amount of charge is the same, independent on the location of the impact on the diode.

Given the insight above, that the pulses behave differently depending on the location of the absorption, we can extract more information from the system. By detecting which type of pulse that is generated by the diode, additional information about the locality of the photon impact can be obtained. This adds information to the image reconstruction procedure. Given this, the receiver chain can be further optimized and additional resolution can be obtained.

Figure 11:
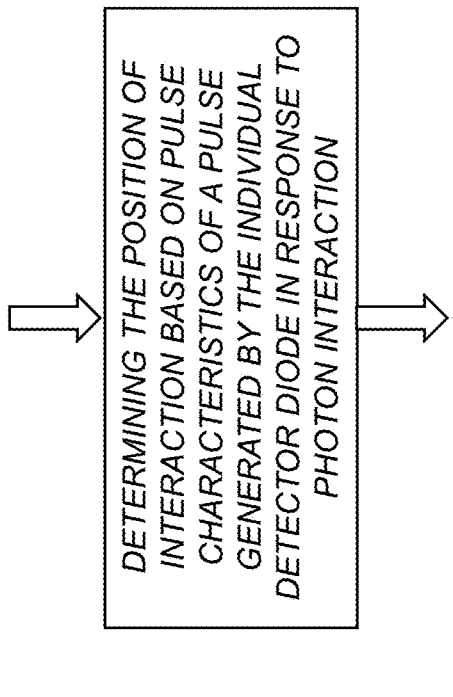
FIG. 11 is a simplified diagram illustrating an example of a method for determining a position of interaction of a photon in an individual detector diode of a photon-counting x-ray detector according to an embodiment.

FIG. 11 is a simplified diagram illustrating an example of a method for determining a position of interaction of a photon in an individual detector diode of a photon-counting x-ray detector according to an embodiment.

Basically, the method is characterized by determining the position of interaction in the detector diode based on pulse characteristics of a pulse generated by the individual detector diode in response to the photon interaction.

By way of example, the position of interaction is determined by performing signal processing of the pulse based on at least one matched filter.

In a particular example, the step of determining the position of interaction in the detector diode comprises:
performing signal processing of the pulse by applying at least one matched filter adapted for a specific pulse type corresponding to a specific position or sub-region of photon interaction in the detector diode, and
identifying whether the pulse matches the pulse type based on the filtered output signal of the matched filter to decide whether the position of interaction corresponds to the specific position or sub-region of the specific pulse type for which the matched filter is adapted.

It should be understood that the term pulse includes any signal representing a pulse, as previously discussed.

As an example, if there is a match according to one or more conditions such as thresholds, e.g. relating to pulse amplitude, pulse width and/or pulse timing, it may be concluded that the position of interaction corresponds to the specific position or sub-region (such as front side) associated with the matched filter. If not, it may for example be decided that the position of interaction corresponds to an opposite or inverse position (such as back side) compared to the specific position or sub-region associated with the matched filter.

Alternatively, the position of interaction may be determined by performing signal processing of the pulse based on at least two matched filters that are configured for mimicking the characteristic responses for different positions or sub-regions of photon interaction in the detector diode.

A basic idea here is therefore to perform signal processing of an incoming pulse from a detector diode to classify the pulse into one of a number of different characteristic pulse types and thereby determine the location of absorption of the incoming photon.

In a particular example, the step of determining the position of interaction in the detector diode comprises:
performing signal processing of the pulse by applying at least two matched filters adapted for different pulse types corresponding to different positions or sub-regions of photon interaction in the detector diode, and
identifying the position of interaction in the detector diode based on the filtered output signals of the matched filters.

As previously indicated, the step of determining the position of interaction in the detector diode may comprise identifying in which one of at least two different sub-regions of the diode the photon interaction occurred based on the pulse characteristics of the pulse.

For example, the detector diode has a thickness corresponding to the width of the diode and the at least two different sub-regions may thus be located in different width sections of the diode.

By way of example, as previously explained, the at least two different regions may comprise a front side or front section and a back side or back section of the diode.

Alternatively, the at least two different regions comprises a front side or front section, a mid-section and a back side or back section of the diode.

It should be understood that the detector diode may be divided into an arbitrary number, N, of sections in the width direction of the diode, each section being associated with a characteristic pulse type.

It should also be understood that the position of interaction may be estimated from the pulse characteristics of the pulse generated at the cathode side or anode side of the detector diode. There is no need to combine pulses from both sides.

As an example, the position of interaction in the detector diode may be determined based on pulse amplitude, pulse width and/or pulse timing.

Figure 12:
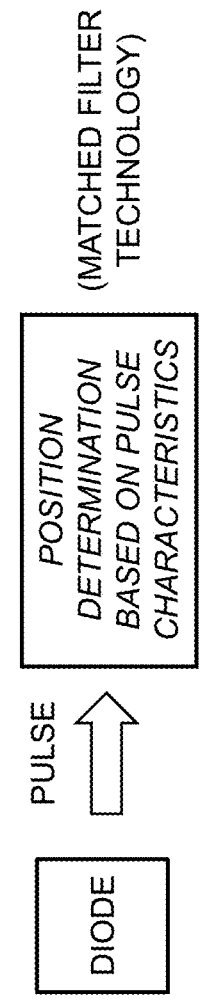
FIG. 12 is a schematic diagram illustrating an example of an arrangement configured to determine a position of interaction of a photon in an individual detector diode of a photon-counting x-ray detector according to an embodiment.

FIG. 12 is a schematic diagram illustrating an example of an arrangement configured to determine a position of interaction of a photon in an individual detector diode of a photon-counting x-ray detector according to an embodiment. Further, the arrangement is configured to determine the position of interaction in the detector diode based on pulse characteristics of a pulse generated by the individual detector diode in response to the photon interaction.

This may for example be accomplished by means of matched filter technology, wherein the arrangement is configured to perform signal processing of the pulse based on at least one matched filter to determine the position of interaction.

In a particular example, the arrangement is configured to perform signal processing of the pulse by applying at least one matched filter adapted for a specific pulse type corresponding to a specific position or sub-region of photon interaction in the detector diode, and identify whether the pulse matches the pulse type based on the filtered output signal of the matched filter to decide whether the position of interaction corresponds to the specific position or sub-region of the specific pulse type for which the matched filter is adapted.

Alternatively, the arrangement is configured to perform signal processing of the pulse based on at least two matched filters that are configured for mimicking the characteristic responses for different positions or sub-regions of photon interaction in the detector diode.

According to another example, the arrangement is configured to perform signal processing of the pulse by applying at least two matched filters adapted for different pulse types corresponding to different positions or sub-regions of photon interaction in the detector diode, and identify the position of interaction in the detector diode based on the filtered output signals of the matched filters.

As an example, the arrangement may be configured to determine the position of interaction in the detector diode by identifying in which one of at least two different sub-regions of the diode the photon interaction occurred based on the pulse characteristics of the pulse.

For example, the detector diode has a thickness corresponding to a width of the diode and the at least two different sub-regions are located in different width sections of the diode. The width sections are typically located between the anode and cathode side of the diode. This may include a front side or front section and a back side or back section of the diode. Alternatively, the at least two different regions comprises a front side or front section, a mid-section and a back side or back section of the diode.

As mentioned, the arrangement may be configured to determine the position of interaction from the pulse characteristics of the pulse generated at the cathode side or anode side of the detector diode.

Also, the arrangement may, as an example, be configured to determine the position of interaction in the detector diode based on pulse amplitude, pulse width and/or pulse timing.

In a particular example, the x-ray detector is a photon-counting edge-on detector.

Figure 1:
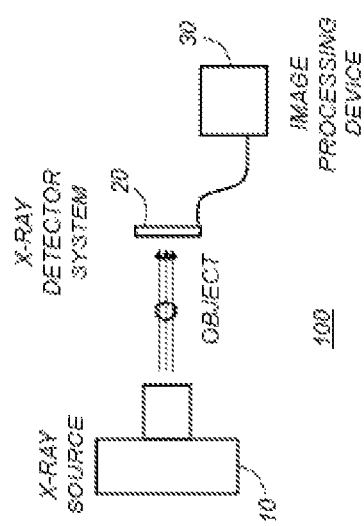
FIG. 1 is a schematic diagram illustrating an example of an overall x-ray imaging system.

According to another aspect, there is provided an x-ray detector system such as that illustrated in FIG. 1 and FIG. 2 comprising such an arrangement.

According to yet another aspect, there is provided an x-ray imaging system such as that illustrated in FIG. 1 and FIG. 2 comprising such an arrangement.

The reference "Energy Calibration of a Silicon-Strip Detector for Photon-Counting Spectral CT by Direct Usage of the X-ray Tube Spectrum", by Xuejin Liu, 2015 describes methods where the receiver can be calibrated for variations in the silicon diode's physical properties. However, the methods described in this reference does not focus on the differences in pulse shapes originating from different sections.

For a better understanding of the proposed technology, a set of non-limiting example embodiments will be described in the following. A suggested procedure to detect the above-mentioned pulses is as follows. In this particular example, the signal processing may be performed in at least two parallel processing paths adapted for capturing or detecting the presence of different pulse types corresponding to different locations of photon impact/interaction. Accordingly, design a filter bank with at least two different signal processing paths, ranging from fast to slow response time, possibly through an optional intermediate path. The fast path will react more quickly to incoming pulses. It will have an electrical filter with signal processing that is optimized for the front-side type of pulses. The slow path will react more slowly to incoming pulses and will have an electrical filter with signal processing that is optimized for the back-side type of pulses.

Figure 13:
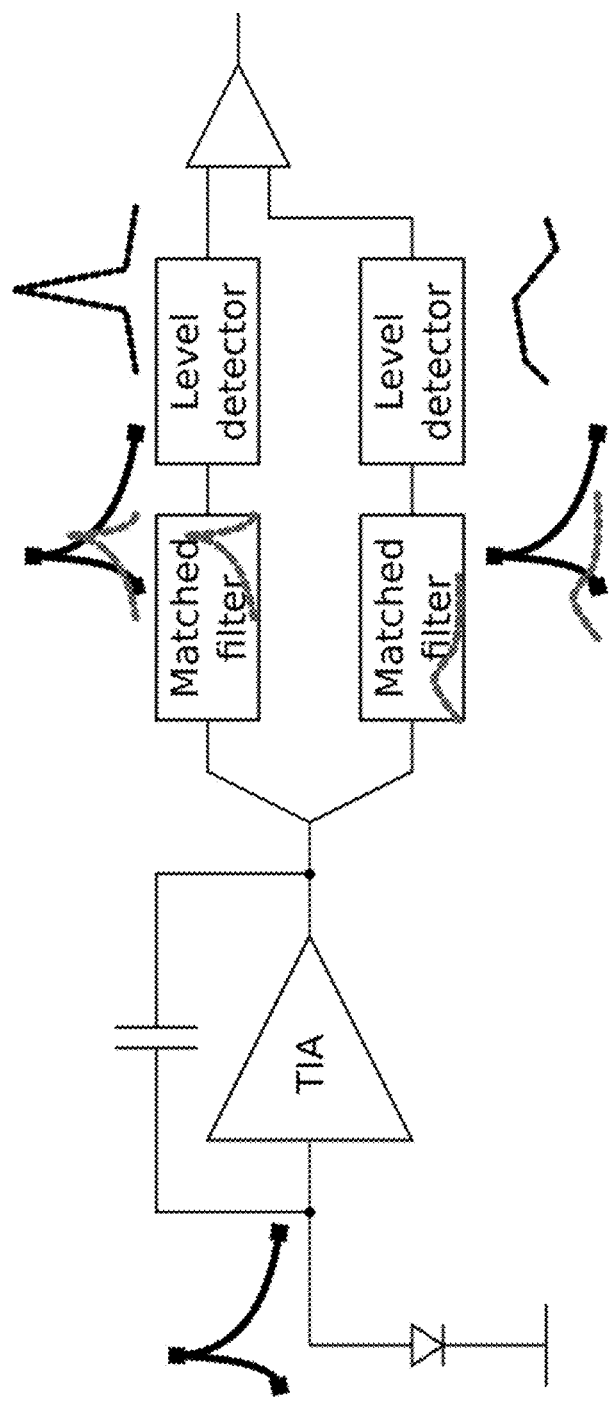
FIG. 13 is a schematic diagram illustrating an example of a simplified version of a receiver front-end for an x-ray pixel or detector diode.

FIG. 13 is a schematic diagram illustrating an example of a simplified version of a receiver front-end for an x-ray pixel or detector diode.

In other words, the circuitry of FIG. 13 represents a relaxed version of a read-out circuit per detector diode. It should be understood that additional filtering and gain adjustments might be used in the read-out path. In this example, the current generated by the detector diode is converted to a voltage through integration on a capacitor with the help of an active Trans-Impedance Amplifier (TIA). The voltage is then copied and filtered through different paths. The black, solid line indicates an incoming front-side pulse type (compare with FIG. 10).

In this example, we use two different paths with two different types of filters. The two filters are designed to have two different types of impulse responses (transfer characteristics) adapted for front-side pulses and back-side pulses. These characteristics are based on the typical behavior from FIG. 10.

In this example, it is suggested to use matched filters where the characteristics of selected types of current pulses (such as front-side pulses and back-side pulses) have been mimicked. By mimicking the pulse waveforms and perform convolution (filter) with the incoming pulse waveform, a filter response can be generated that is optimum in a maximum-likelihood sense. It is assumed that we generate a set of typical filters with the following impulse response:

$$h(t)=q(T-t) \quad (2)$$

where $q(t)$ is a template of the pulse $p(t)$ generated by the diode, trying to look as equal as possible. In the ideal case $q(t)=p(t)$ in a reasonably long period of time. Among linear filters, matched filters are known to be the optimal to increase the signal-to-noise ratio (SNR) under the presence of noise.

The output $y(t)$ of the matched filter will be given by the convolved result:

$$y(t)=\int h(\tau) \cdot p(t-\tau)d\tau = \int q(T-\tau) \cdot p(t-\tau)d\tau \quad (3)$$

which, if q and p align well, will be a symmetrical function with a comparatively distinct peak amplitude, highest voltage/current, at around time point T (after the pulse has arrived at the detector input). The linear filtering operation performs an auto-correlation operation on the pulse, i.e., the input pulse is correlated/matched to a template waveform. The more they match, the higher the amplitude of $y(t)$ at T will be. The more they match, the shorter—in time—the peak will be. In the schematic diagram of FIG. 13, this is indicated with a peak for the upper-most path where the impulse response of the filter matches the incoming pulse better. The other path shows a smoother response. In this example, the processing path adapted for detecting a front-side pulse will detect the peak of the filtered front-side pulse at least based on amplitude, but possibly also based on pulse timing, whereas the processing path adapted for detecting a back-side pulse will likely not detect any distinctive peak of the filtered front-side pulse. Consequently, the front-side processing path will react and provide a positive response indicating that the considered pulse is a front-side pulse. Consequently, it can be determined that the corresponding photon-interaction took place on the front side of the detector element's diode.

In practice, this means that by using appropriately configured matched filters adapted for selected pulse types and a subsequent pulse identifying module (e.g. employing one or more level detectors), the locality of absorption of the photon can be determined with higher resolution than normal.

Not only the amplitude is relevant, but also the pulse timing and/or pulse length, as can be seen from the characteristic pulse types of FIG. 10. This means that detection of a certain type of pulse can be performed by signal processing based on pulse amplitude, pulse timing and/or pulse length. For example, a certain amount of knowledge about peak amplitudes, peaking time and/or pulse length can be extracted from the characteristic pulses shown in FIG. 10.

This means that the different paths will give quite distinctly different signals (voltages/currents) and the inventors have recognized the possibility of detecting the differences between the paths to enable the determination of which received pulse is the most likely one. The use of appropriate filters such as matched filters will emphasize the distinction and make it easier to detect the different types of pulses.

Figure 14:
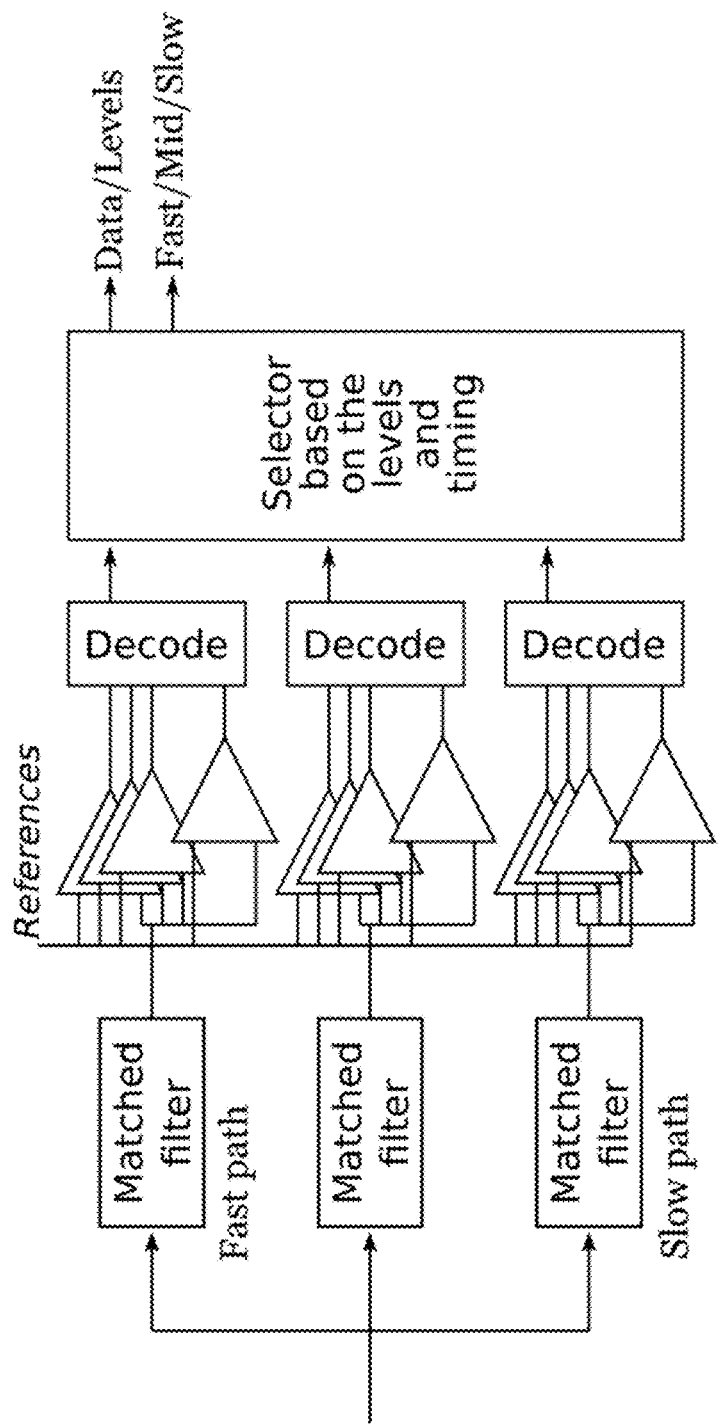
FIG. 14 is a schematic diagram illustrating an example of a more elaborate version of a bank of filters for an example of three processing path according to an embodiment.

FIG. 14 is a schematic diagram illustrating an example of a more elaborate version of a bank of filters for an example of three processing path according to an embodiment. A set of comparators is used to compare the pulses to different thresholds to provide for energy-resolving multi-bin operation. With the help of the comparators we are able to detect the amount of energy and duration in each pulse. The comparators will "slice" the pulses in a number of levels producing a corresponding set of digitized waveforms representing the pulse.

Further on, we are able to locally compare the results and thereby judge which is the most likely received pulse and forward that information—together with the basic count and level data—to a digital image processing system and/or processor. It may be sufficient to choose data from only one path.

The embodiment of FIG. 14 is an example of an implementation by duplication of signal path with different types of filters. Duplicating the paths will however come with an increased cost of hardware. Especially the high-speed comparators are expensive in terms of area and power consumption.

Figure 15:
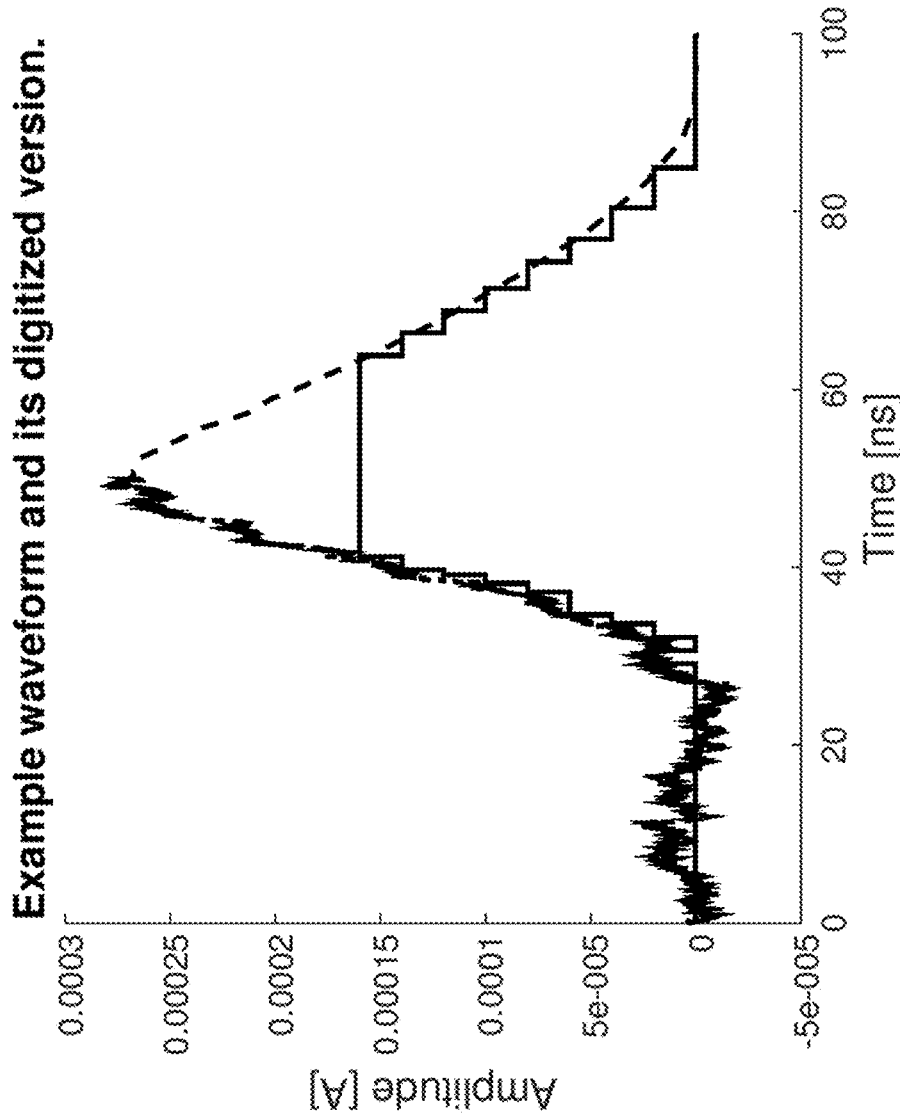
FIG. 15 is a schematic diagram illustrating an example of a waveform and its digitized waveform generated using the comparators of FIG. 14.

FIG. 15 is a schematic diagram illustrating an example of a waveform and its digitized waveform generated using the comparators of FIG. 14.

Figure 16:
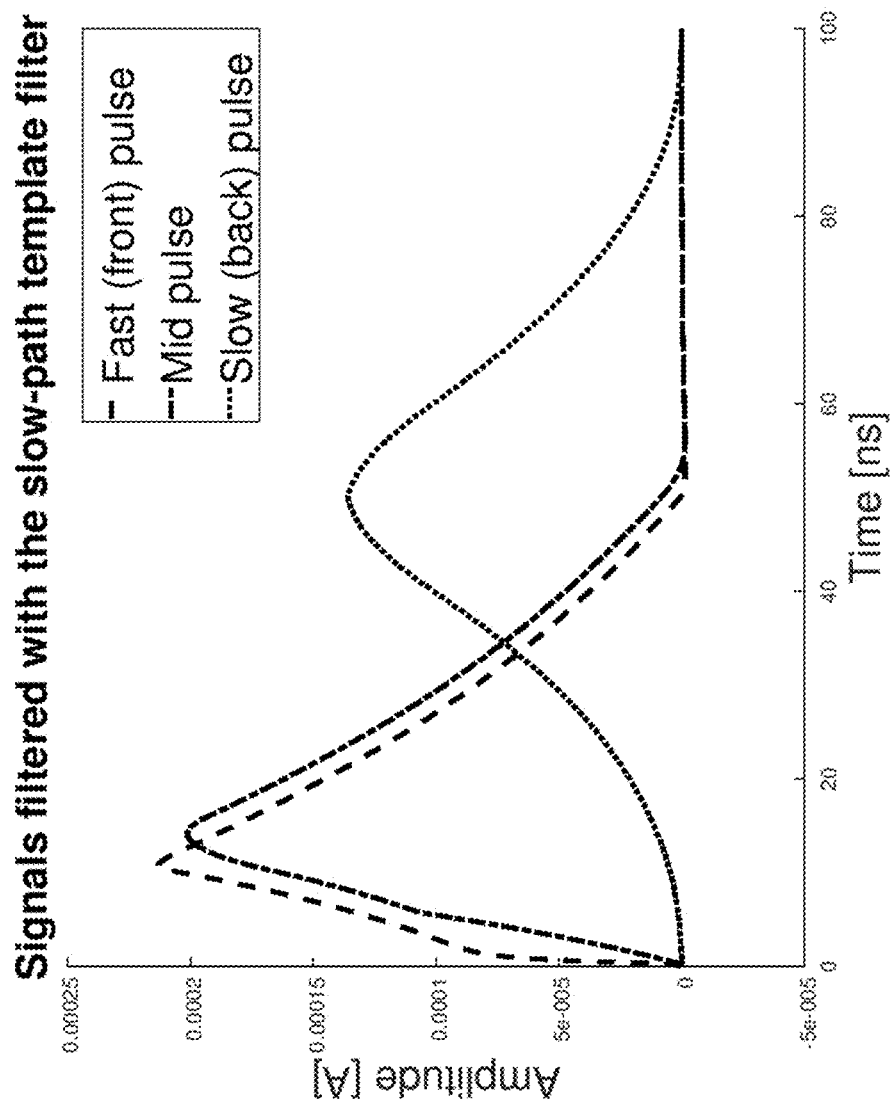
FIG. 16 shows the matched filter responses when processing three different pulse types (fast pulse, mid pulse and slow pulse) in a slow path (using a slow-path template filter) adapted for a slow (back-side) pulse type.
Figure 17:
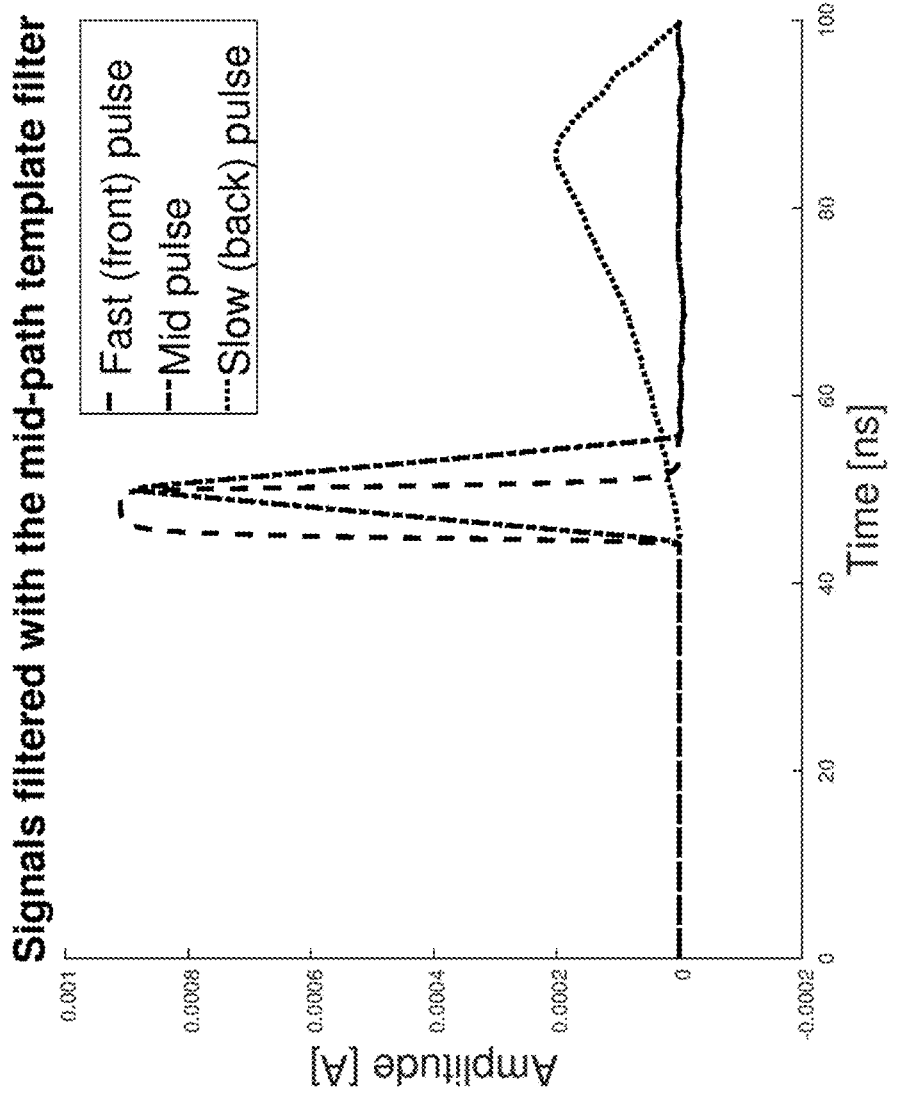
FIG. 17 shows the matched filter responses when processing three different pulse types (fast pulse, mid pulse and slow pulse) in a mid-path (using a mid-path template filter) adapted for a mid-section pulse type.
Figure 18:
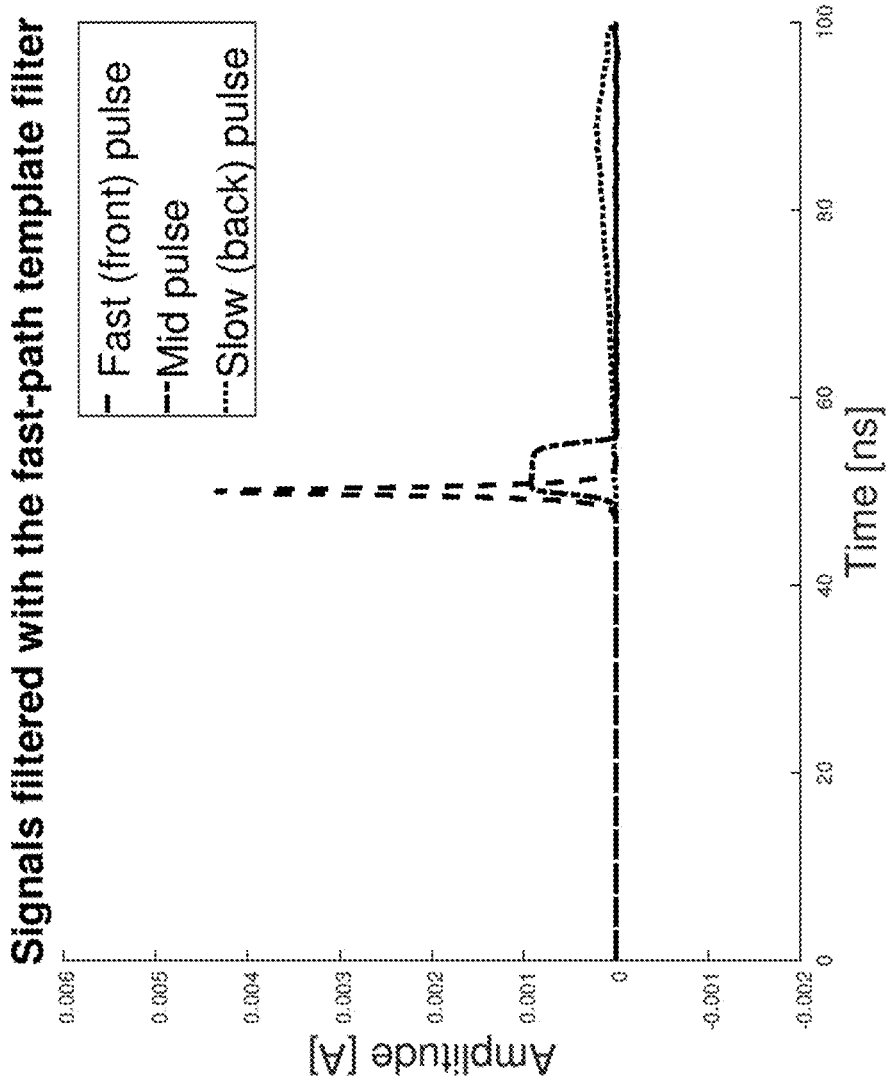
FIG. 18 shows the matched filter responses when processing three different pulse types (fast pulse, mid pulse and slow pulse) in a fast path (using a fast-path template filter) adapted for a fast (front-side) pulse type.

FIG. 16, FIG. 17 and FIG. 18 are schematic diagrams illustrating a plot of the original waveforms (front, mid, back) as filtered by the three different filters, e.g. corresponding to the configuration of FIG. 14. These figures illustrate the different possible scenarios that could occur in the sensor. Overall, there are nine typical different waveforms. Instantaneously, only one type of pulse enters the read-out circuit and is filtered through all three paths. The incoming pulses have been normalized, i.e., showing the same amount of charge. Notice that the y-axes are not to same scale in the three figures.

FIG. 16 shows the matched filter responses when processing three different pulse types (fast pulse, mid pulse and slow pulse) in a slow path (using a slow-path template filter) adapted for a slow (back-side) pulse type.

FIG. 17 shows the matched filter responses when processing three different pulse types (fast pulse, mid pulse and slow pulse) in a mid-path (using a mid-path template filter) adapted for a mid-section pulse type.

FIG. 18 shows the matched filter responses when processing three different pulse types (fast pulse, mid pulse and slow pulse) in a fast path (using a fast-path template filter) adapted for a fast (front-side) pulse type.

The matched filter response for a slow (back-side) pulse is indicated by dotted lines, whereas the matched filter response for a mid-section pulse is indicated by dash-dotted lines, and the matched filter response for a fast (front-side) pulse is indicated by dashed lines.

For example, for FIG. 16, a slow back-side pulse is sent through a slow path filter to produce the dotted curve, and a mid-section pulse is sent through the same slow path filter to produce the dashed curve and a fast front-side pulse is sent through the same slow path filter to produce the semi-solid curve.

Within each figure, we see how the filtered signals show different behaviors, which when characterized, may be useful in distinguishing between the different pulse types.

In FIG. 16, notice that the pulses are similar (but taking their maximum values at different time points). However, the matched response of the slow back-side pulse (dotted line) is distinctly different from the others in pulse timing, pulse width and pulse amplitude. A procedure for determining the different pulse types may for example be based on pulse amplitude, pulse width and/or pulse timing.

In FIG. 17, the slow back-side pulse (dotted) is once again distinctly different in shape, amplitude and position in time. The matched response of the mid pulse (dash-dotted) shows a sharper peak behavior than the fast front pulse (dashed). Here, pulse amplitude, width and/or timing may be used to distinguish the different pulse types.

In FIG. 18, the matched response of the fast front-side pulse is clearly distinct (dashed) compared to the other waveforms. All three filtered pulse are easily distinguished by amplitude, width and/or timing.

Figure 19:
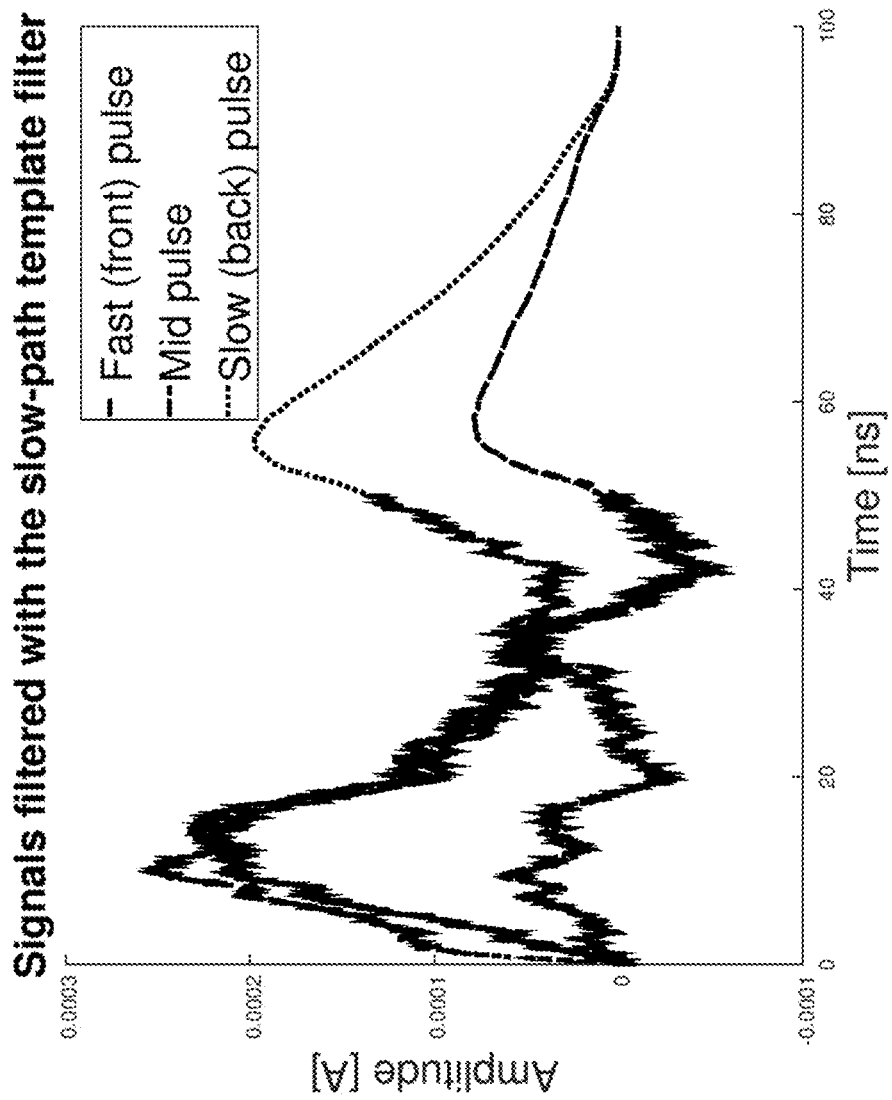
FIG. 19 is a schematic diagram showing an example of the matched filter responses using a slow-path template filter in the presence of significant noise.
Figure 20:
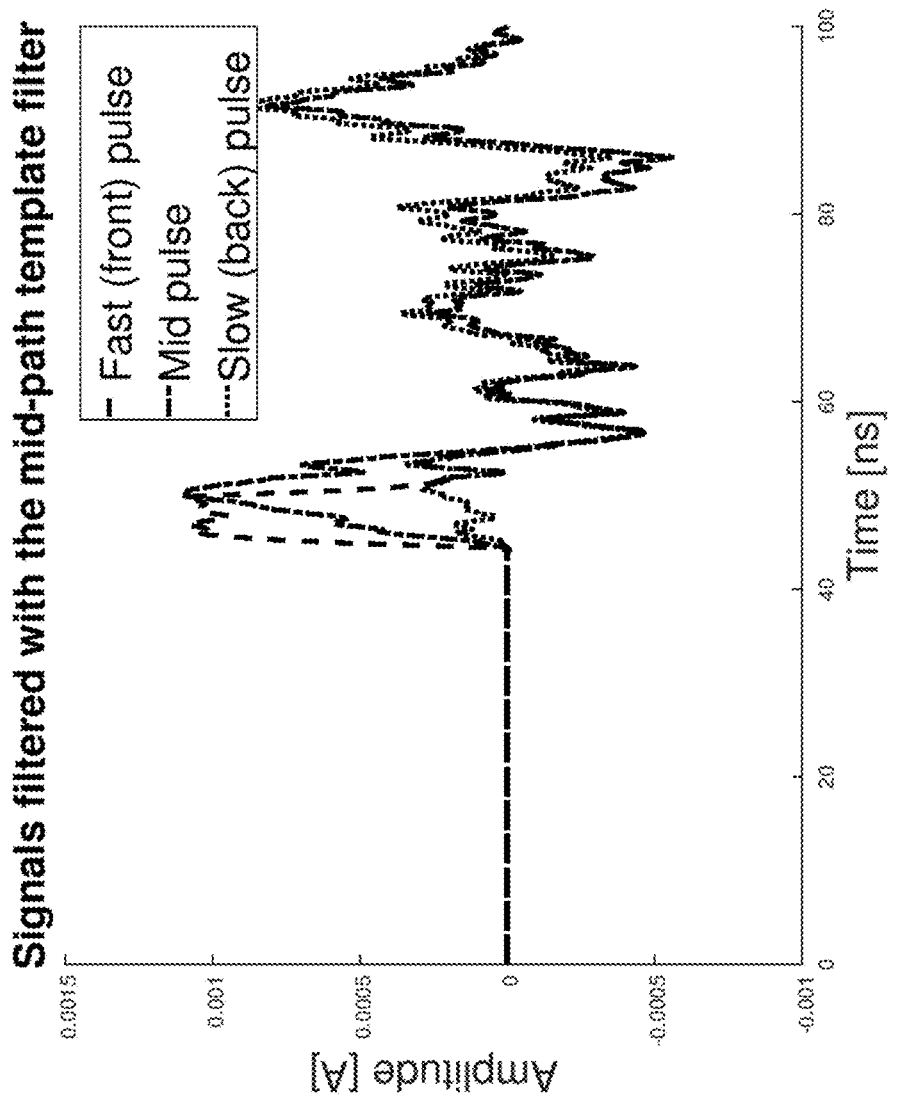
FIG. 20 is a schematic diagram showing an example of the matched filter responses using a mid-path template filter in the presence of significant noise.
Figure 21:
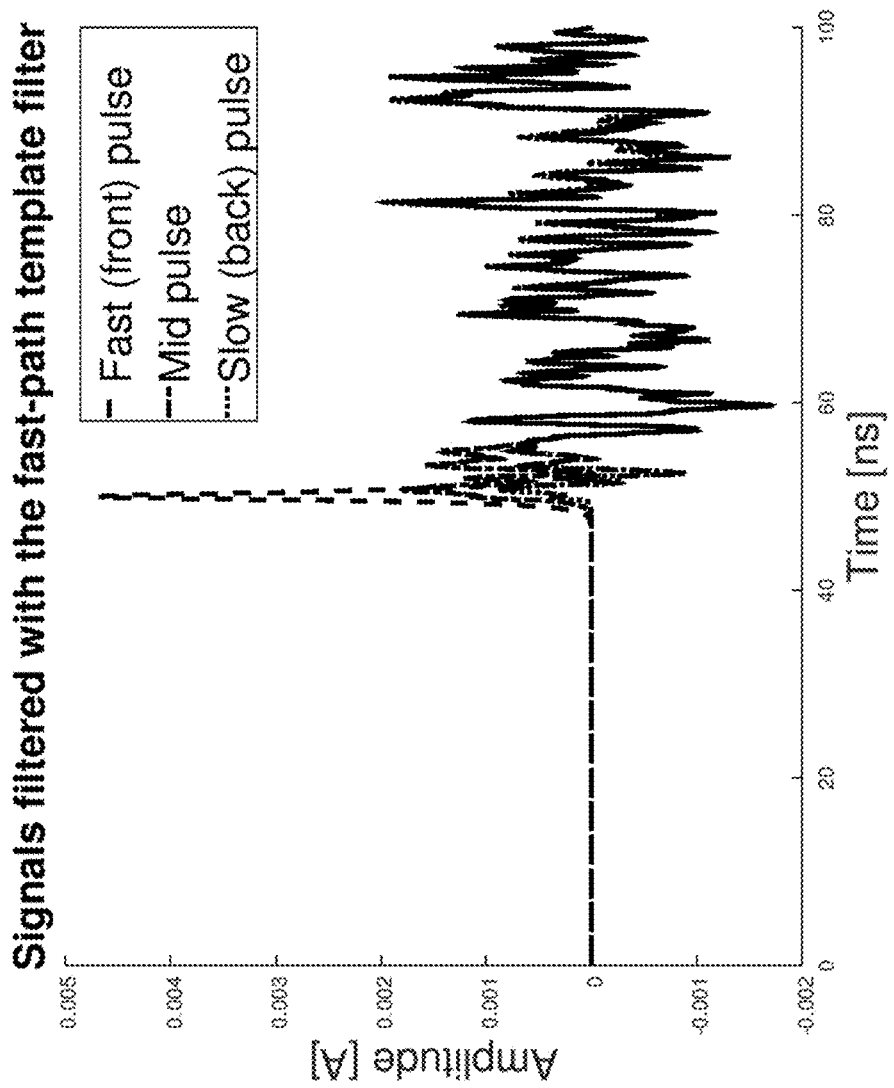
FIG. 21 is a schematic diagram showing an example of the matched filter responses using a fast-path template filter in the presence of significant noise.

FIG. 19, FIG. 20 and FIG. 21 are schematic diagrams illustrating examples of the matched filtered responses in the presence of significant noise.

FIG. 19 is a schematic diagram showing an example of the matched filter responses using a slow-path template filter in the presence of significant noise. The matched response of the slow back-side pulse shows a higher amplitude in the later part of the measured time interval.

FIG. 20 is a schematic diagram showing an example of the matched filter responses using a mid-path template filter in the presence of significant noise.

FIG. 21 is a schematic diagram showing an example of the matched filter responses using a fast-path template filter in the presence of significant noise.

Noise is added to the input signal, mimicking noise in the diode, and not the matched filter as such, i.e., assuming circuit noise to be zero, which is why we see "clean" signals on one side of the waveforms. We have added same current noise for all types of input pulses in order to be able to compare them.

Similarly to above, there are differences in the behavior of the fast and slow cases, and it seems possible to detect a fast pulse with the fast filter and a slow pulse with the slow filter, even in the presence of significant noise. With this level of noise, it seems to be more difficult to identify any pattern in the midsection part of the pixel given the test signals we are displaying here.

With matched filters we increase the noise immunity compared to just using a set of filter banks with different time constants, although it should be understood that the latter may also be an acceptable solution.

Since we have access to the information from all paths simultaneously, it is also possible to combine them to extract which one has passed through which. In the diagrams discussed above, the mid and front-side pulses look very similar in the slow path. They look however increasingly different in the other paths. It is the same with the slow back-side pulse; notice how it more or less looks like noise in the fast path, but shows a distinct peak in the slow path. The filtered matched response of the back-side pulse is typically slower, peaking at a later point in time than the other pulses with a larger pulse width. The filtered matched response of the front-side pulse is typically faster, with a higher amplitude and a more narrow, distinct peak. Utilizing this type of analysis, by designing a type of maximum likelihood detector that observes the data generated by the reference comparators, i.e., the shape of the pulses.

It is understood that the hardware will increase significantly if the reference level comparators are big in component size. It may therefore be desirable to reduce the hardware by actively switching between the paths and sharing the comparators (connected to the references).

Figure 22:
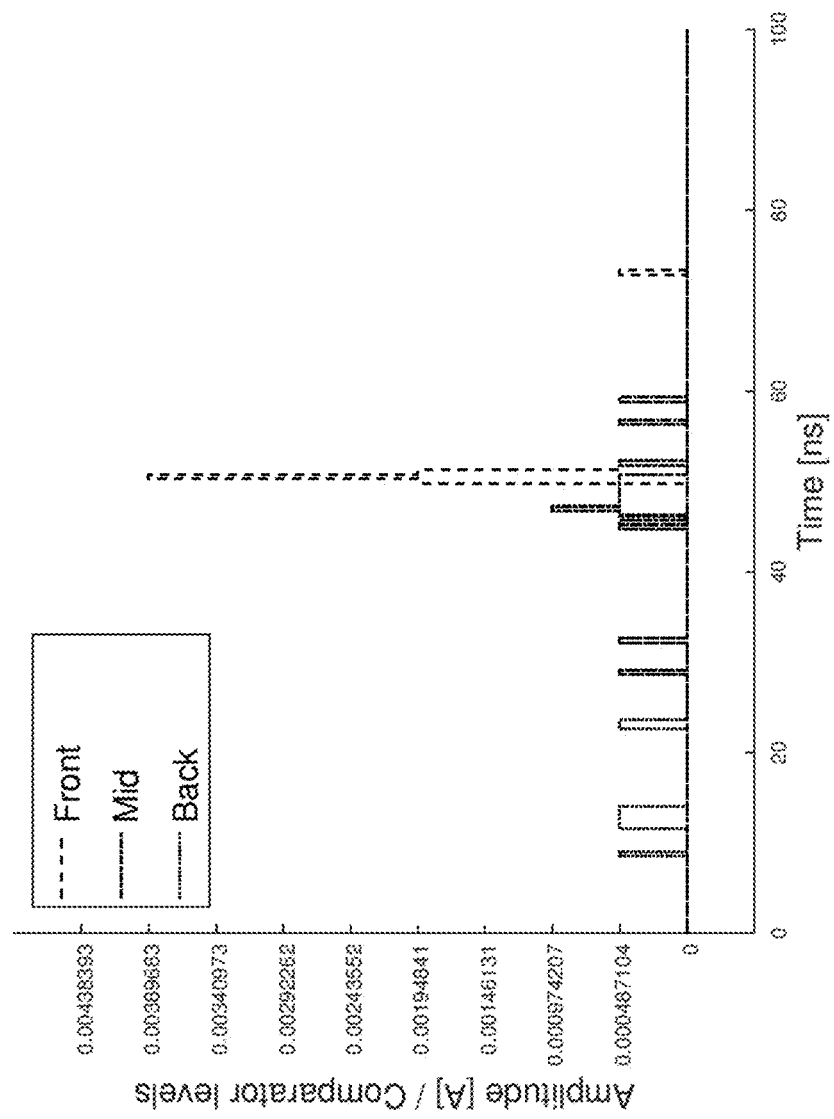
FIG. 22 shows the filter responses of a fast front-side pulse in each of the three template filters; front-side filter (fast path), mid filter (middle path) and back-side filter (slow path).
Figure 23:
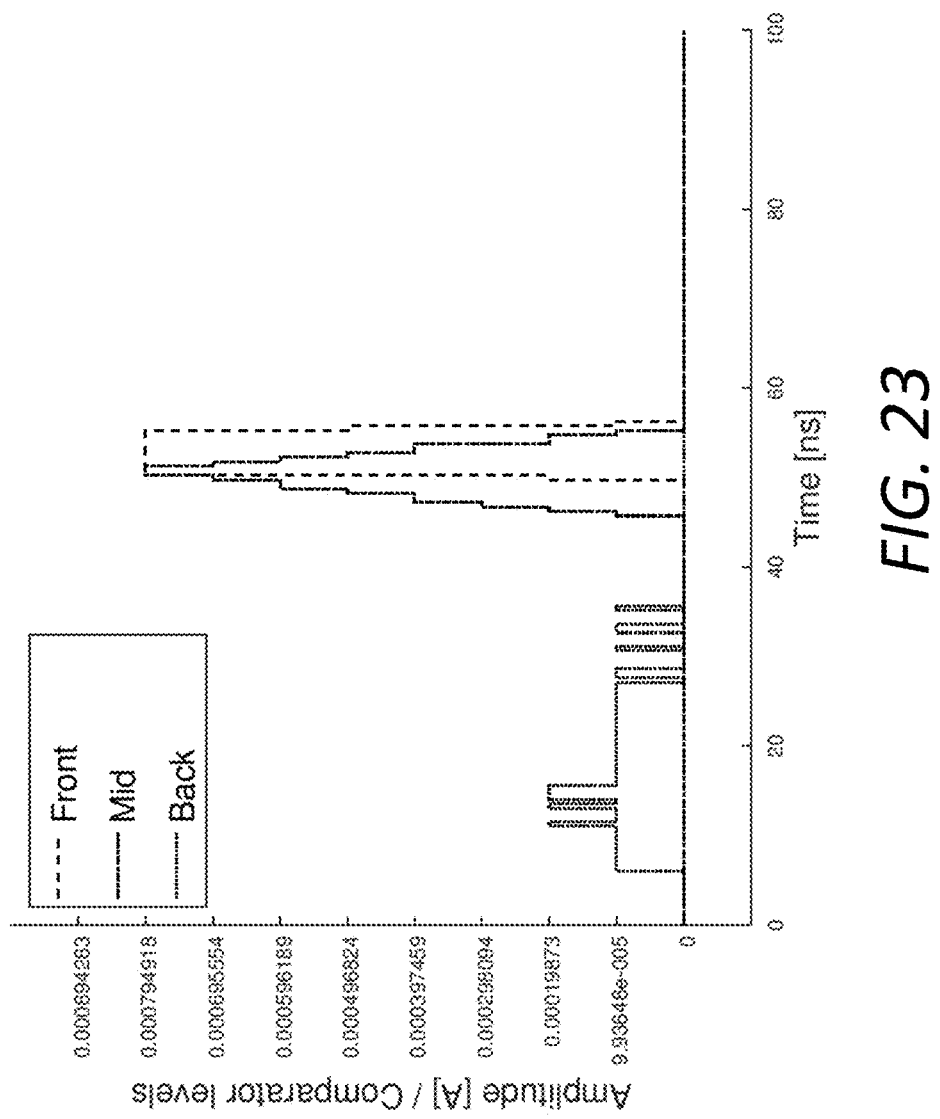
FIG. 23 shows the filter responses of a mid-pulse in each of the three template filters; front-side filter (fast path), mid filter (middle path) and back-side filter (slow path).
Figure 24:
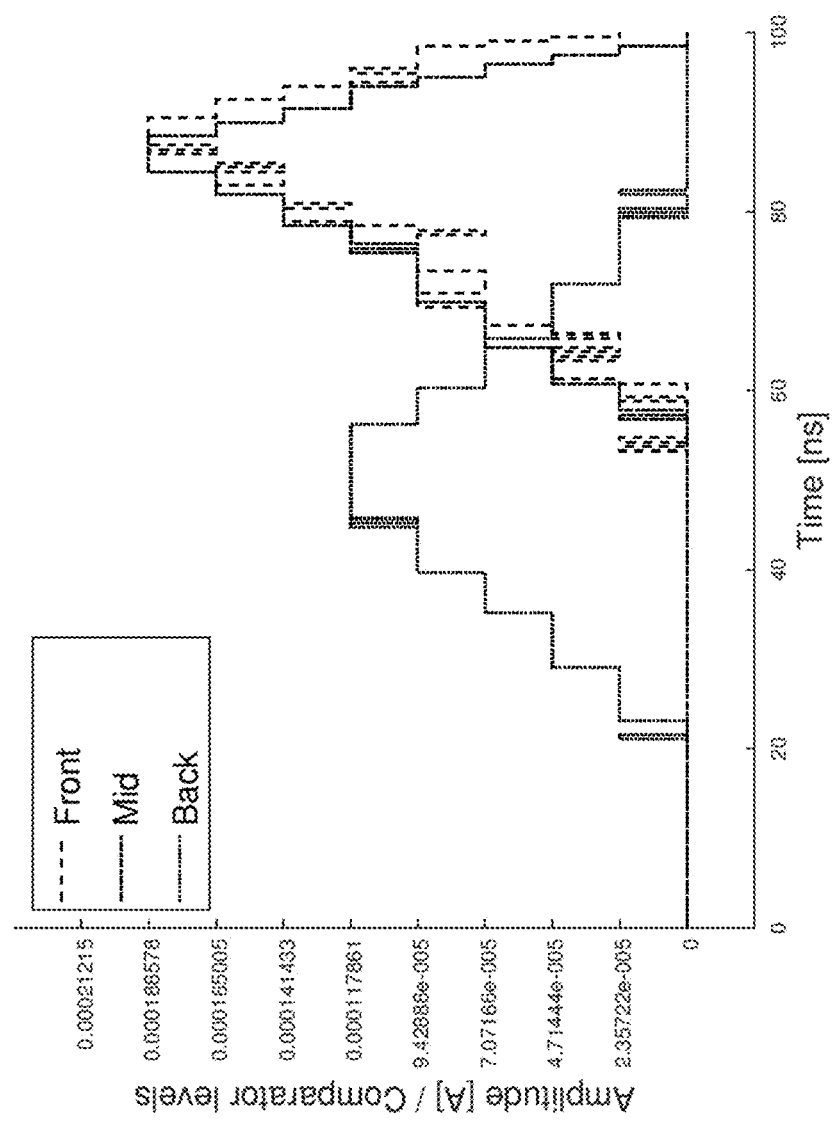
FIG. 24 shows the filter responses of a slow back-side pulse in each of the three template filters; front-side filter (fast path), mid filter (middle path) and back-side filter (slow path).

FIG. 22, FIG. 23 and FIG. 24 are schematic diagrams illustrating examples of the digitized outputs from the three filters, respectively, for three different types of input signals. Noise is added both on the diode (detector input) and in the filters (analog circuit noise). Thresholds for the comparators are dynamically adjusted for the paths. Handles for these thresholds are provided to the host processor which controls the thresholds based on the image quality.

FIG. 22 shows the filtered responses for three different types of pulses, front-side pulse (dashed), mid-pulse (dash-dotted) and back-side pulse (dotted), through the fast filter.

FIG. 23 shows the filtered responses for three different types of pulses, front-side pulse (dashed), mid-pulse (dash-dotted) and back-side pulse (dotted), through the mid filter.

FIG. 24 shows the filtered responses for three different types of pulses, front-side pulse (dashed), mid-pulse (dash-dotted) and back-side pulse (dotted), through the slow filter.

Example Pseudo Code

An illustrative example of a simple pseudo algorithm to identify the pulses is given below. In this example, the decision is based on pulse amplitude, but it should be understood that pulse timing and/or pulse width may also be used. The decision parameters are fuzzy, but the algorithm is in this case designed to give a Boolean type response. It could however be designed to provide the host with a probability of the detected pulse without significant increase in complexity.

```
IF (peak ampl in fast path) SIGNIFCANTLY_HIGHER_THAN (peak
ampl in other paths) THEN
    detected_pulse = "FRONT-SIDE"
ELSE    ## Slow or mid?
    IF (peak ampl in slow path) APPROX_EQUAL_TO (peak
    ampl in other paths) THEN
        detected_pulse = "BACK-SIDE"
    ELSE
        detected_pulse = "MID-SECTION"
```

Example Simulation Results

Figure 26:
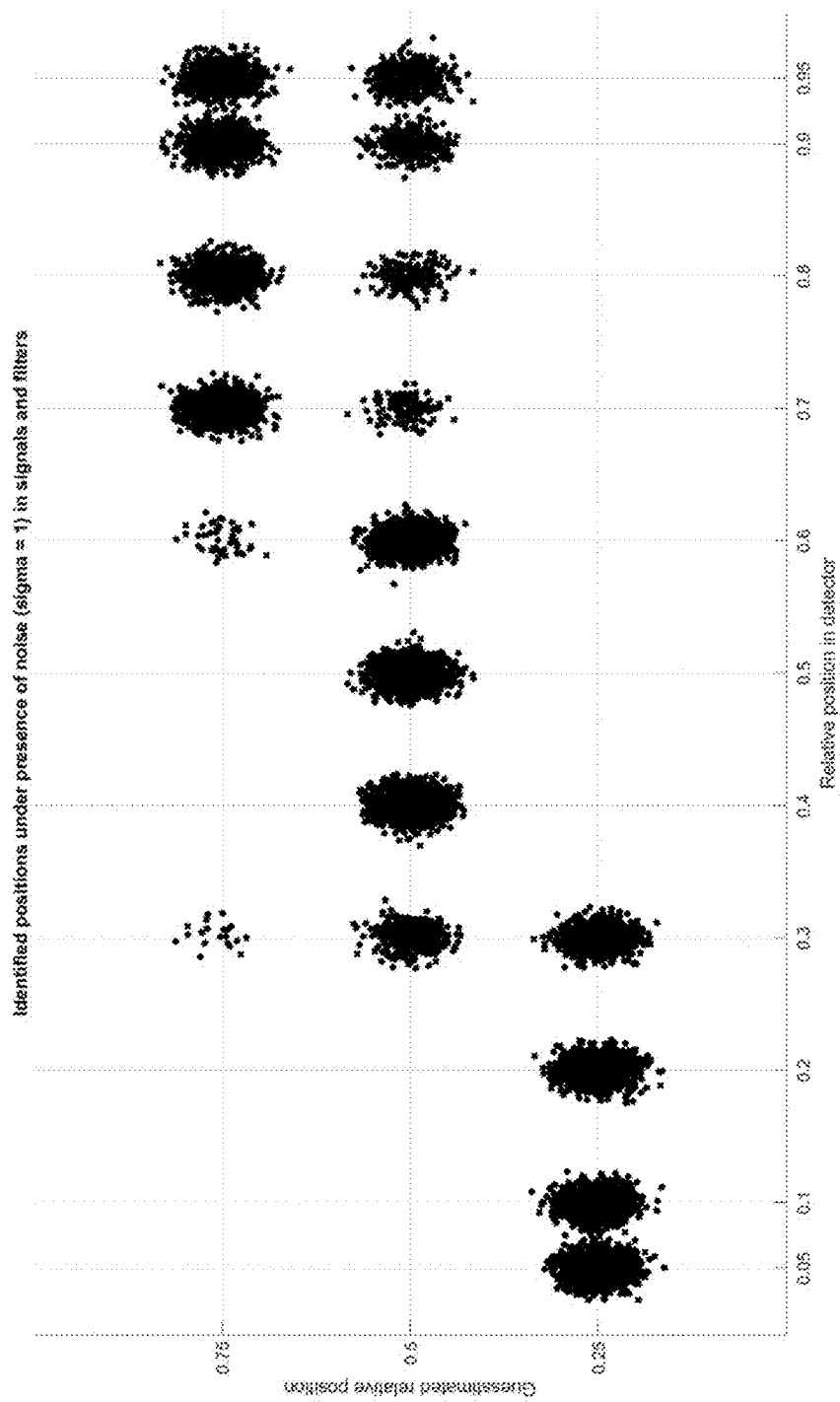
FIG. 26 is a schematic diagram illustrating an example of simulation results showing simulated detection noise added to the input pulses and the filtering path(s).
Figure 27:
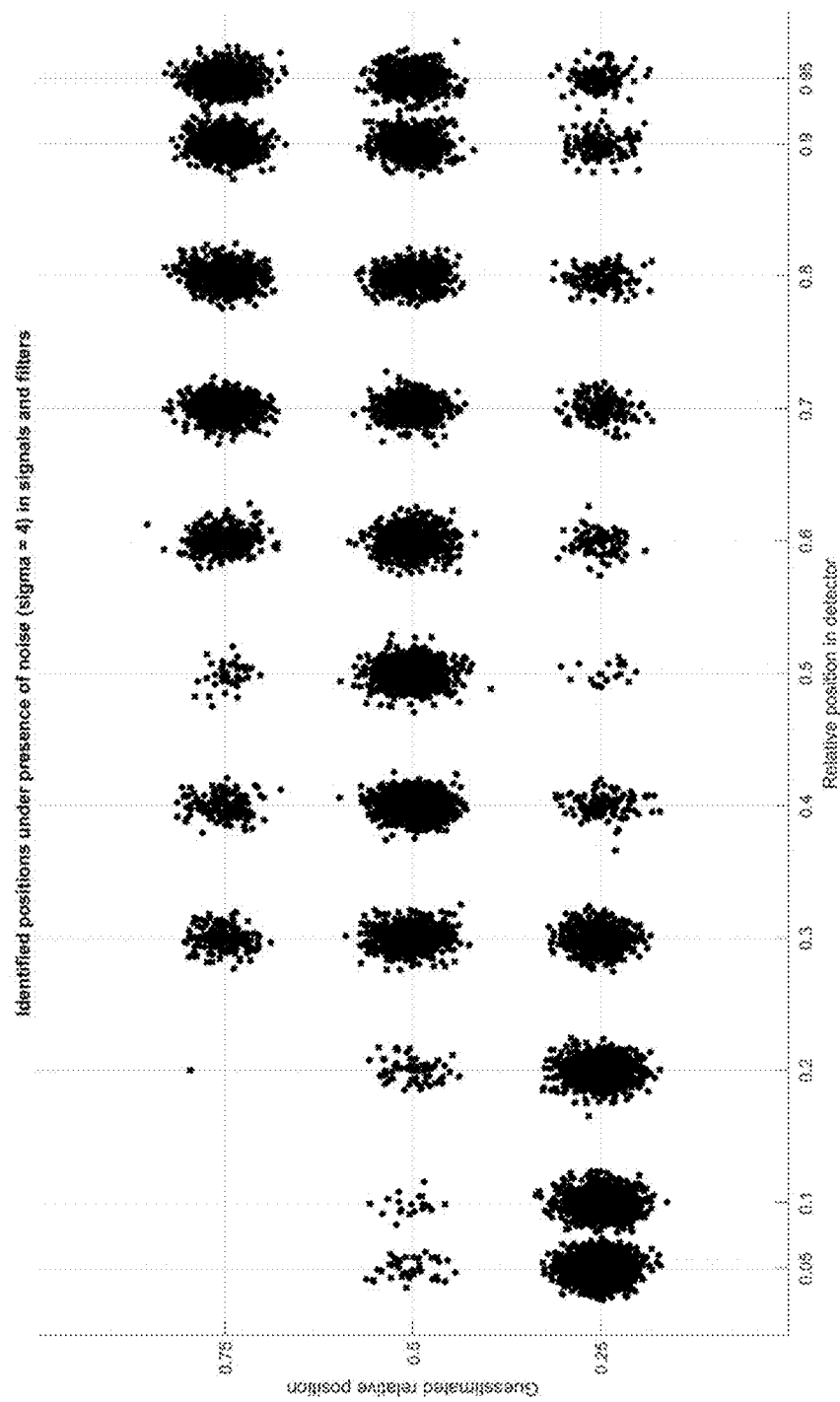
FIG. 27 is a schematic diagram illustrating an example of simulation results showing simulated detection with a noise level higher than the input signal levels.

Using the simple pseudo-code presented above with three filters in parallel, we are able to detect the origin of the incidents to a certain degree. The simulation results of FIG. 25, FIG. 26 and FIG. 27 show how the improved detector identifies the locations.

Along the x axis, we find the position of the incident photon (see FIG. 9), where "0" indicates the closer end and "1" indicates the far end of the detector diode.

Along the y axis, we find the estimated position given the pseudo code presented above. In the simulation examples we use a detector that can identify three positions, i.e., within 0 to 33% (front section), 33% to 67% (mid-section) and 67% to 100% (back section).

Figure 25:
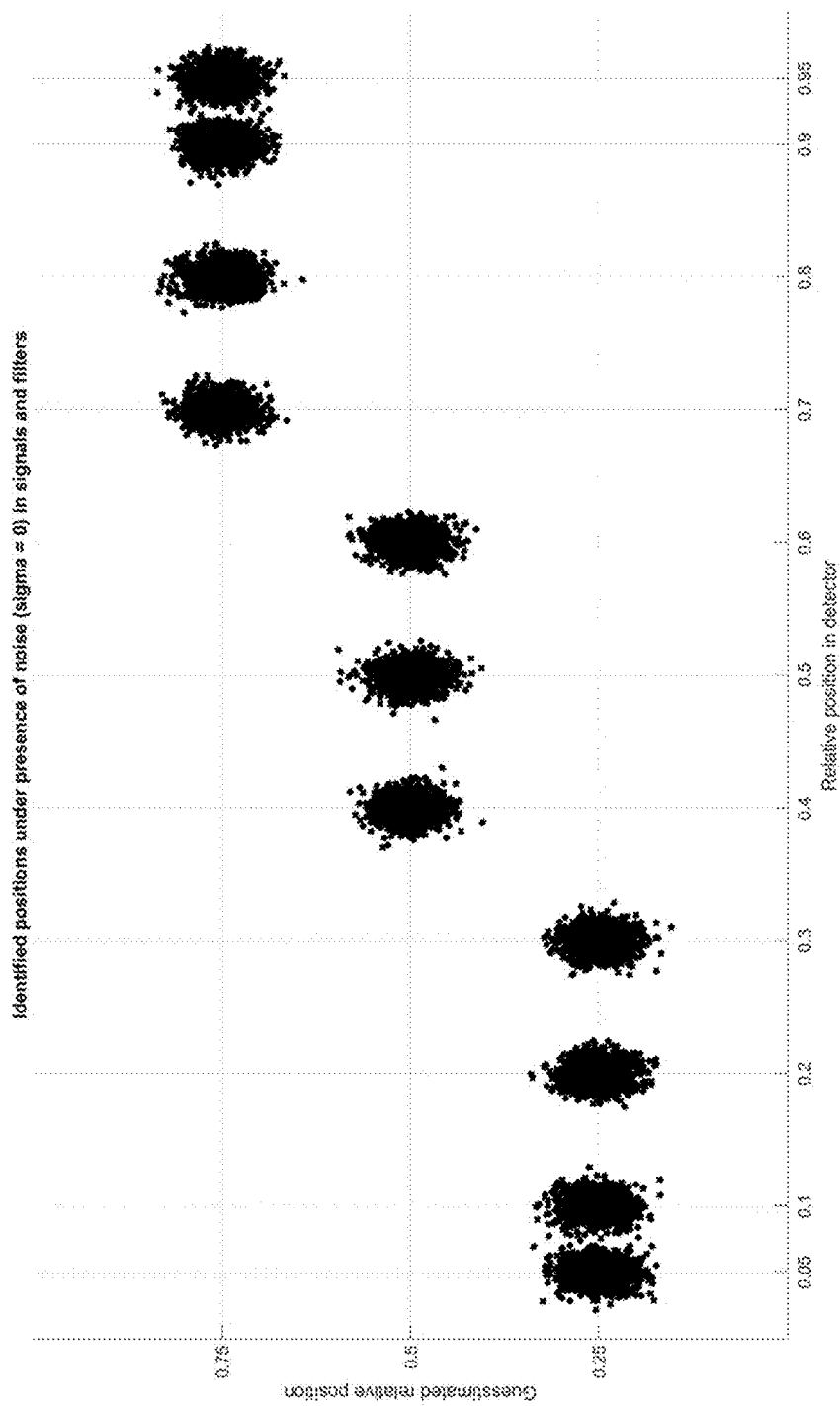
FIG. 25 is a schematic diagram illustrating an example of simulation results showing simulated detection with no noise present.

FIG. 25 is a schematic diagram illustrating an example of simulation results showing simulated detection with no noise present. In the example of FIG. 25, we have not added any noise to the signal nor filters. We have deliberately added a Gaussian random deviation to the location of the points in the graphs to allow for the thickness/intensity of the clouds, to indicate the probability of the detected positions.

FIG. 26 is a schematic diagram illustrating an example of simulation results showing simulated detection noise added to the input pulses and the filtering path(s). The noise level is quite substantial compared to the amplitudes of the input pulses; noise in parity with input signal levels. We see that some errors in the detections are found. Here the intensity of the clouds indicates how often they are detected correctly.

FIG. 27 is a schematic diagram illustrating an example of simulation results showing simulated detection with a noise level higher than the input signal levels. In FIG. 27, we have increased the noise further and we see that even though the detection becomes less efficient, the detection procedure still can—to a certain probability—identify positions in the detector.

Figure 28:
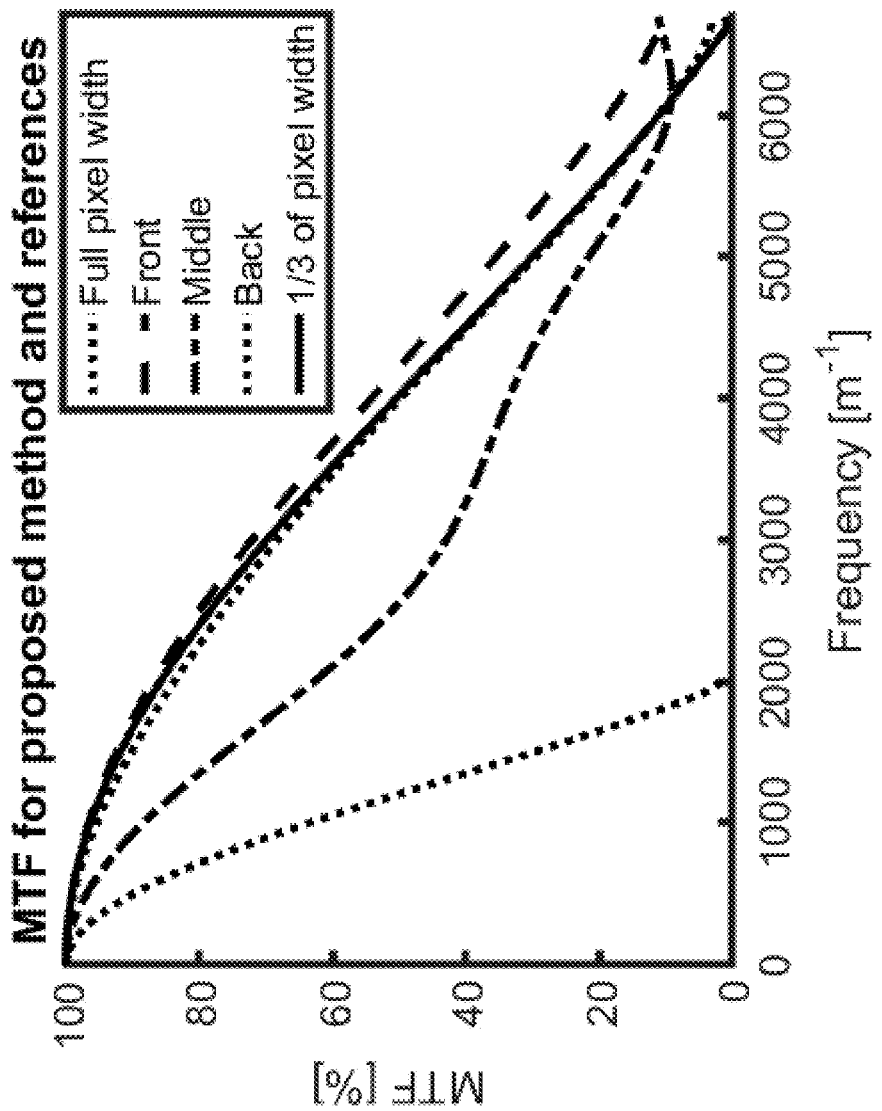
FIG. 28 is a schematic diagram illustrating the Modulation Transfer Function (MTF) for the proposed methodology and comparative references.

FIG. 28 is a schematic diagram illustrating the Modulation Transfer Function (MTF) for the proposed methodology and comparative references according to simulations.

In FIG. 28, the MTF is illustrated for the example simulation results discussed above. The MTF is the modulation transfer function for pictures reconstructed from the detector elements (diodes, pixels) in the detector. The MTF describes how good the resolution is in the picture. Along the x axis we have the spatial frequency, i.e., how well a full transition from a black to a white pixel can be resolved. For example, the 3000 value indicates that 3000 cycles black/white can be resolved per meter. The y axis indicates how off we are from the full scale values. A value of 100% indicates we reach black level and white level completely. A value of 0% indicates that we will get stuck in an average gray level and there will be no difference between "white" and "black"—just a gray average. The ideal behavior would be 100% over all frequencies. Most realistic implementations of vision systems drop monotonically from 100% down to 0%.

In the simulations we have used the values above for a normalized noise level of sigma=1, where there are significant amounts of "faulty detections" using the pseudo-code algorithm, i.e., significant error sources are incorporated in the simulations.

Assuming we have one detector element (diode, pixel) and one read-out circuit per detector element (diode, pixel) and no identification of the sub-regions, i.e., a pixel of full dimension, this hardware scenario will give us an MTF as the dotted left-most curve, i.e., the one dropping to 0% for f=2000 (Dotted "Full pixel width"). This will serve as an original reference for comparison with the present invention.

Assume now we could divide the detector element (diode, pixel) into three detector elements (diodes, pixels) (i.e., more hardware and smaller pixels) and have one read-out circuit per each, i.e., we define a new detector with three times the resolution. The impact on hardware is significant in many ways and a very costly solution, if possible at all. This scenario, however, is simulated and plotted as the solid line ("⅓ of pixel width") and is also used as a comparison with the others.

With the approach suggested in this invention we get the dashed, dashed-dotted and right-most dotted lines ("Front", "Middle", and "Back"). Notice that the dotted, right-most line is almost overlapping the solid "⅓ of pixel width" line.

It is evident from FIG. 28 that the new estimations ("Front", "Middle", and "Back") are more accurate in terms of resolution compared to the original, left-most dotted line (i.e., "Full pixel width"). On average (assuming we observe "Front"+"Back"+"Middle")/3, although not explicitly plotted in FIG. 28) the performance is close to the desired physical ⅓ performance.

Taking an MTF quality value of 40%, we see that the proposed method improves the pixel resolution by a factor of 2-3 (200-300%) compared to the original scenario and to the benefit of not having to implement too small pixels. This is truly a significant improvement.

There are some known system designs that conceptually approach similar problems, but with different solutions.

For example, U.S. Pat. No. 6,169,287 relates to an x-ray detector method and apparatus for obtaining spatial, energy, and/or timing information using signals from neighboring electrodes in an electrode array. The detector and corresponding method are based on having a multitude of detector strips and for every x-ray incident, the currents from several strips are used to deduce the position.

U.S. Pat. No. 7,009,183 relates to a gamma-ray detector and mentions detecting the position of interaction based on the results from several strips in the detector, but without disclosing any particular method for doing so.

In clear contrast, the present invention investigates the signal from an individual detector element (one strip only) and analyzes the signal in a very different way by employing matched filters mimicking the characteristic response for different incident positions. In applications with relatively high count rates, it is not possible to use signals from several strips since there would be pile-up from several events, and the receivers would be saturated. A remedy would be to use much smaller strips (to minimize the probability for many incidents in same strip), but it would be impractical from an implementation point of view.

U.S. Pat. No. 7,208,740 relates to a three-dimensional radiation detector for PET or SPECT applications. A three-dimensional spatial resolution is obtained by having many small detector voxels and detecting the signal in each of them.

This is however inverse to the present invention, where signal processing is used to determine the position of interaction in the detector, especially to keep the number of required voxels low. Too many voxels increase the power consumption significantly and would also increase the production cost.

U.S. Pat. No. 7,692,155 relates to a three-dimensional, position-sensitive radiation detection by observing and studying the time drift of the detected signal. They focus on calibrating the system by finding characteristic delay times. In clear contrast, the present invention aims at detecting the location and use that for enhanced image processing.

It will be appreciated that the methods and devices described herein can be combined and re-arranged in a variety of ways.

For example, embodiments may be implemented in hardware, or in software for execution by suitable processing circuitry, or a combination thereof.

The steps, functions, procedures, modules and/or blocks described herein may be implemented in hardware using any conventional technology, such as discrete circuit or integrated circuit technology, including both general-purpose electronic circuitry and application-specific circuitry.

Particular examples include one or more suitably configured digital signal processors and other known electronic circuits, e.g. discrete logic gates interconnected to perform a specialized function, or Application Specific Integrated Circuits (ASICs). It should also be understood that a combination of analog and digital processing circuitry may be used.

Alternatively, at least some of the steps, functions, procedures, modules and/or blocks described herein may be implemented in software such as a computer program for execution by suitable processing circuitry such as one or more processors or processing units.

Examples of processing circuitry includes, but is not limited to, one or more microprocessors, one or more Digital Signal Processors (DSPs), one or more Central Processing Units (CPUs), acceleration hardware, and/or any suitable programmable logic circuitry such as one or more Field Programmable Gate Arrays (FPGAs), or one or more Programmable Logic Controllers (PLCs).

It should also be understood that it may be possible to re-use the general processing capabilities of any conventional device or unit in which the proposed technology is implemented. It may also be possible to re-use existing software, e.g. by reprogramming of the existing software or by adding new software components.

FIG. 29 is a schematic diagram illustrating an example of a computer implementation according to an embodiment. In this particular example, the system 200 comprises a processor 210 and a memory 220, the memory comprising instructions executable by the processor, whereby the processor is operative to perform the steps and/or actions described herein. The instructions are typically organized as a computer program 225; 235, which may be preconfigured in the memory 220 or downloaded from an external memory device 230. Optionally, the system 200 comprises an input/output interface 240 that may be interconnected to the processor(s) 210 and/or the memory 220 to enable input and/or output of relevant data such as input parameter(s) and/or resulting output parameter(s).

The term 'processor' should be interpreted in a general sense as any system or device capable of executing program code or computer program instructions to perform a particular processing, determining or computing task.

The processing circuitry including one or more processors is thus configured to perform, when executing the computer program, well-defined processing tasks such as those described herein.

The processing circuitry does not have to be dedicated to only execute the above-described steps, functions, procedure and/or blocks, but may also execute other tasks.

The proposed technology also provides a computer-program product comprising a computer-readable medium 220; 230 having stored thereon such a computer program.

By way of example, the software or computer program 225; 235 may be realized as a computer program product, which is normally carried or stored on a computer-readable medium 220; 230, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program may thus be loaded into the operating memory of a computer or equivalent processing device for execution by the processing circuitry thereof.

The method flows presented herein may be regarded as a computer action flows, when performed by one or more processors. A corresponding device, system and/or apparatus may be defined as a group of function modules, where each step performed by the processor corresponds to a function module. In this case, the function modules are implemented as a computer program running on the processor. Hence, the device, system and/or apparatus may alternatively be defined as a group of function modules, where the function modules are implemented as a computer program running on at least one processor.

The computer program residing in memory may thus be organized as appropriate function modules configured to perform, when executed by the processor, at least part of the steps and/or tasks described herein.

Alternatively it is possibly to realize the modules predominantly by hardware modules, or alternatively by hardware. The extent of software versus hardware is purely implementation selection.

The embodiments described above are merely given as examples, and it should be understood that the proposed technology is not limited thereto. It will be understood by those skilled in the art that various modifications, combinations and changes may be made to the embodiments without departing from the present scope as defined by the appended claims. In particular, different part solutions in the different embodiments can be combined in other configurations, where technically possible.

The invention claimed is:

1. A method for determining a position of interaction of a photon in an individual detector diode of a photon-counting edge-on x-ray detector having detector diodes extending in the depth direction of the photon-counting edge-on x-ray detector, assuming an x-ray enters through an edge of the photon-counting edge-on x-ray detector, each individual detector diode of the detector diodes having a thickness, in a direction substantially perpendicular to the depth direction, corresponding to a width of the individual detector diode, the method comprising:
determining the position of interaction in the line of thickness of the individual detector diode by identifying, in which one sub-region of at least two different sub-regions of the individual detector diode, photon interaction occurred, based on pulse characteristics of a pulse generated by the individual detector diode in response to the photon interaction,
wherein the at least two different sub-regions are located in different width sections of the individual detector diode, and the width sections are located between an anode and a cathode of the detector diode.

2. The method of claim 1, wherein the position of interaction is determined by performing signal processing of the pulse based on at least one matched filter.

3. The method of claim 1, wherein the determining the position of interaction in the individual detector diode comprises:
performing signal processing of the pulse by applying at least one matched filter configured for a specific pulse type corresponding to a specific position or sub-region of photon interaction in the individual detector diode to generate a filtered output signal of the at least one matched filter, and
identifying whether the pulse matches the pulse type based on the filtered output signal of said at least one matched filter to decide whether the position of interaction corresponds to the specific position or sub-region of the specific pulse type for which said at least one matched filter is configured.

4. The method of claim 1, wherein the position of interaction is determined by performing signal processing of the pulse based on at least two matched filters that are configured to mimic characteristic responses for different positions or sub-regions of photon interaction in the individual detector diode.

5. The method of claim 1, wherein the determining the position of interaction in the individual detector diode comprises:
performing signal processing of the pulse by applying at least two matched filters configured for different pulse types corresponding to different positions or sub-regions of photon interaction in the individual detector diode to generate filtered output signals of the matched filters, and
identifying the position of interaction in the individual detector diode based on the filtered output signals of the matched filters.

6. The method of claim 1, wherein the at least two different regions comprise a front side or a front section and a back side or a back section of the individual detector diode.

7. The method of claim 1, wherein the at least two different regions comprise a front side or a front section, a mid-section, and a back side or a back section of the individual detector diode.

8. The method of claim 1, wherein the position of interaction is estimated from the pulse characteristics of the pulse generated at the cathode or the anode of the individual detector diode.

9. The method of claim 1, wherein the position of interaction in the individual detector diode is determined based on pulse amplitude, pulse width, and/or pulse timing.

10. A system configured to determine a position of interaction of a photon in an individual detector diode of a photon-counting edge-on x-ray detector having detector diodes extending in the depth direction of the photon-counting edge-on x-ray detector, assuming an x-ray enters through an edge of the photon-counting edge-on x-ray detector, each individual detector diode of the detector diodes having a thickness, in a direction substantially perpendicular to the depth direction, corresponding to a width of the individual detector diode, the system comprising:
one or more processors configured to determine the position of interaction in the line of the thickness of the individual detector diode by identifying, in which one sub-region of at least two different sub-regions of the individual detector diode, photon interaction occurred, based on pulse characteristics of a pulse generated by the individual detector diode in response to the photon interaction,
wherein the at least two different sub-regions are located in different width sections of the individual detector diode, and the width sections are located between an anode and a cathode of the detector diode.

11. The system of claim 10, wherein the one or more processors is configured to perform signal processing of the pulse based on at least one matched filter to determine the position of interaction.

12. The system of claim 10, wherein the one or more processors is configured to perform signal processing of the pulse by applying at least one matched filter configured for a specific pulse type corresponding to a specific position or sub-region of photon interaction in the individual detector diode to generate a filtered output signal of the at least one matched filter, and identify whether the pulse matches the pulse type based on the filtered output signal of said at least one matched filter to decide whether the position of interaction corresponds to the specific position or sub-region of the specific pulse type for which said at least one matched filter is configured.

13. The system of claim 10, wherein the one or more processors is configured to perform signal processing of the pulse based on at least two matched filters that are configured to mimic characteristic responses for different positions or sub-regions of photon interaction in the individual detector diode.

14. The system of claim 10, wherein the one or more processors is configured to perform signal processing of the pulse by applying at least two matched filters adapted for different pulse types corresponding to different positions or sub-regions of photon interaction in the individual detector diode to generate filtered output signals of the matched filters, and identify the position of interaction in the individual detector diode based on the filtered output signals of the matched filters.

15. The system of claim 10, wherein the at least two different regions comprises a front side or front section and a back side or back section of the diode.

16. The system of claim 10, wherein the at least two different regions comprise a front side or front section, a mid-section, and a back side or a back section of the individual detector diode.

17. The system of claim 10, wherein the one or more processors is configured to determine the position of interaction from the pulse characteristics of the pulse generated at the cathode or the anode of the individual detector diode.

18. The system of claim 10, wherein the one or more processors is configured to determine the position of interaction in the individual detector diode based on pulse amplitude, pulse width, and/or pulse timing.

19. An x-ray detector system comprising:
the system of claim 10.

20. An x-ray imaging system comprising:
the system of claim 10.

* * * * *